US009486432B2

(12) United States Patent
Washington

(10) Patent No.: US 9,486,432 B2
(45) Date of Patent: *Nov. 8, 2016

(54) COMPOSITIONS AND METHODS FOR TREATING MACULAR DEGENERATION

(71) Applicant: The Trustees of Columbia University in the City of New York, New York, NY (US)

(72) Inventor: Ilyas Washington, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/510,975

(22) Filed: Oct. 9, 2014

(65) Prior Publication Data
US 2015/0133549 A1 May 14, 2015

Related U.S. Application Data

(62) Division of application No. 12/733,631, filed as application No. PCT/US2008/010676 on Sep. 12, 2008, now Pat. No. 8,877,809.

(60) Provisional application No. 60/993,379, filed on Sep. 12, 2007.

(51) Int. Cl.
*A61K 31/135* (2006.01)
*A61K 31/215* (2006.01)
*A61K 31/167* (2006.01)
*A61K 45/06* (2006.01)

(52) U.S. Cl.
CPC ........... *A61K 31/215* (2013.01); *A61K 31/135* (2013.01); *A61K 31/167* (2013.01); *A61K 45/06* (2013.01)

(58) Field of Classification Search
CPC . A61K 31/135; A61K 31/215; A61K 31/167
See application file for complete search history.

(56) References Cited

U.S. PATENT DOCUMENTS

| | | | |
|---|---|---|---|
| 5,310,764 A | 5/1994 | Baranowitz et al. |
| 6,660,297 B2 | 12/2003 | Bartels et al. |
| 7,566,808 B2 | 7/2009 | Rando |
| 8,124,646 B2 | 2/2012 | Liu |
| 8,263,601 B2 | 9/2012 | Tung et al. |
| 2002/0012966 A1 | 1/2002 | Shi et al. |
| 2002/0169176 A1 | 11/2002 | Elder et al. |
| 2003/0032078 A1 | 2/2003 | Travis |
| 2003/0149997 A1 | 8/2003 | Hageman |
| 2004/0009907 A1 | 1/2004 | Alsobrook et al. |
| 2004/0121407 A1 | 6/2004 | Distefano et al. |
| 2004/0235113 A1 | 11/2004 | Shi et al. |
| 2005/0059010 A1 | 3/2005 | Stone et al. |
| 2005/0119536 A1 | 6/2005 | Hageman |
| 2005/0176662 A1 | 8/2005 | Inana et al. |
| 2005/0220768 A1 | 10/2005 | McVey et al. |
| 2005/0256207 A1 | 11/2005 | McGrath |
| 2006/0089411 A1 | 4/2006 | Gierhart |
| 2006/0094063 A1 | 5/2006 | Mata et al. |
| 2006/0099714 A1 | 5/2006 | Mata et al. |
| 2006/0135460 A1 | 6/2006 | Widder et al. |
| 2006/0292099 A1 | 12/2006 | Milburn et al. |
| 2007/0014833 A1 | 1/2007 | Milburn et al. |
| 2007/0015827 A1 | 1/2007 | Widder et al. |
| 2007/0135481 A1 | 6/2007 | Jordan et al. |

FOREIGN PATENT DOCUMENTS

| | | |
|---|---|---|
| JP | H10513197 A | 12/1998 |
| JP | 2002275095 A | 9/2002 |
| JP | 2004526725 A | 9/2004 |
| JP | 2006526662 A | 11/2006 |
| WO | 9504018 B1 | 2/1995 |
| WO | 9624344 A1 | 8/1996 |
| WO | 02072528 B2 | 9/2002 |
| WO | 2005000230 A2 | 1/2005 |
| WO | 2005065669 B3 | 7/2005 |
| WO | 2005087210 A2 | 9/2005 |
| WO | 2007019503 A2 | 2/2007 |

OTHER PUBLICATIONS

Sakai, et al. "Ocular Age Pigment 'A2-E': An Unprecedented Pyridinium Bisretinoid," J. Am. Chem. Soc. (1996), vol. 118, pp. 1559-1560.
Schutt, et al. "Accumulation of A2-E in mitochondrial membranes of cultured RPE cells," Graefe's Arch. Clin. Exp. Ophthalmol. (2007), vol. 245, pp. 391-398.
Schutt, et al. "Photodamage to human RPE cells by A2-E, a retinoid component of lipofuscin," Invest. Ophthalmol. Vis. Sci. (2000), vol. 41, pp. 2303-2308.
Shaban, et al., "A2E and blue light in the retina: the paradigm of age-related macular degeneration," Bioi. Chem. (2002), vol. 383, pp. 537-545.
Shaban, et al., "Phosphatidylglycerol potently protects human retinal pigment epithelial cells against apoptosis induced by A2E, a compound suspected to cause age-related macula degeneration," Exp. Eye Res. (2002), vol. 75, pp. 99-108.
Smith, "Autofluorescence characteristics of early, atrophic, and high-risk fellow eyes in age-related macular degeneration," Invest Ophthalmol Vis Sci. (2006), vol. 47, pp. 5495-5504.

(Continued)

*Primary Examiner* — Zohreh Fay
(74) *Attorney, Agent, or Firm* — McCarter & English, LLP; Steven G. Davis; Mei Bai

(57) ABSTRACT

Methods of retarding formation of a lipofuscin pigment in the retina and of treating or ameliorating the effects of a disease characterized by an accumulation of a lipofuscin pigment in a retina are provided. These methods include the step of administering to a patient in need thereof a substituted $C_{20}$-retinoid in an amount sufficient to reduce accumulation of a lipofuscin pigment in the retina. Further provided are methods of retarding formation of A2E and/or ATR-dimer by replacing an all-trans-retinal (ATR) substrate with a $C_{20}$-$D_3$-retinal substrate under conditions sufficient to impede the formation of A2E. Compositions for retarding formation of a lipofuscin pigment in the retina containing a substituted $C_{20}$-retinoid and a pharmaceutically acceptable carrier are also provided.

28 Claims, 15 Drawing Sheets

(56) References Cited

OTHER PUBLICATIONS

Um, et al. "Synthesis and Biological Activity of Novel Retinamide and Retinoate Derivatives," Chemical & Pharmaceutical Bulletin (2004), vol. 52, pp. 501-506.

Soriatane, [online], [retrieved Jul. 5, 2012] Retrieved from RXList: The Internet Drug Index using Internet <URL: http://www.rxlist.com/cgi/generic/acitretin.htm>.

Sparrow, et al. A2E, a Lipfuscin Fluorophore, in Human Retinal Pigmented Epithelial Cells in Culture, Invest. Ophthamol Vis Sci (1999), vol. 40, pp. 2988-2995.

Sparrow, et al. "The lipofuscin fluorophore A2E mediates blue light-induced damage to retinal pigmented epithelial cells," Invest. Ophthamol. Vis. Sci. (2000), vol. 41, pp. 1981-1989.

Sparrow, et al., "A2E-epoxides damage DNA in retinal pigment epithelial cells. Vitamin E and other antioxidants inhibit A2E-epoxide formation," J. Biol. Chem. (2003), vol. 278, pp. 18207-18213.

Sreekumar et al. "Protection from oxidative stress by methionine sulfoxide reductases in RPE cells," Biochem Biophys Res Commun (2005), vol. 334:1, pp. 245-253.

Suter, et al. "Age-related Macular Degeneration: The lipofuscin component n-retinyl-n-retinylidene ethanolamine detaches proapoptotic proteins from mitochondria and induces apoptosis in mammalian retinal pigment epithelial cells," J. Bio. Chem. (2000), vol. 275, pp. 39625-39630.

Targretin, [online], [retrieved Jul. 5, 2012] Retrieved from RXlist: The Internet Drug Index using Internet <URL: http://www.rxlist.com/cgi/generic/bexarotene.htm>.

Toth, "Functional changes of the aging rat retina in relation to the modifications of the ERG components," Aktuelle Gerontol (1976), vol. 6, pp. 79-86.

Travis, G. H. et al., Diseases caused by defects in the visual cycle: retinoids as potential therapeutic agents, Annual Review of Pharmacology and Toxicology, Annual Review Inc., Palo Alto, CA (2007), vol. 47, pp. 469-512 (NIH Public Access Author manuscript, pp. 1-38).

Villablanca, et al. "Phase I trial of 13-cis-retinoic acid in children with neuroblastoma following bone marrow transplantation," J Clin Oncol. (1995), vol. 13, pp. 894-901.

Wassell, et al. "A role for vitamin A in the formation of ocular lipofuscin," Br J Ophthalmol (1997), vol. 81, pp. 911-918.

Watson, et al. "Comparison of low-vision reading with spectacle-mounted magnifiers," J. Rehabil Res Dev. (2005), vol. 42:4, pp. 459-470.

Weng, et al. "Insights into the function of Rim protein in photoreceptors and etiology of Stargardt's disease from the phenotype in abcr knockout mice," Ce// (1999), vol. 98, pp. 13-23.

Wright, et al. "Hybrid eye tracking for computer-aided retinal surgery," Biomed Sci Instrum (1996), vol. 32, pp. 225-235.

Walker, "New/Old Findings on Unique Vitamin E," [online], [retrieved on Sep. 5, 2012] retrieved from the Internet: <http://www.enerex.ca/en/articles/new-old-findings-on-unique-vitamin-e.htm>.

Japanese Office Action with English translation from counterpart Japanese Application No. 2012-260971 dated Feb. 7, 2014.

"What is Deuterium?" [retrieved on 2/1112013], <URL: http://www.innovateus.net/printfscience/what-deuterium>. 4 pages.

Foster, Allan, "Deuterium Isotope Effects in Studies of Drug Metabolism," TIPS—Dec. 1984.

Handelman et al., "An Improved Protocol for Determining Ratios of Retinol-d4 to Retinol Isolated from Human Plasma", Anal. Chem. (1993), vol. 65, pp. 2024-2028.

Haskins, N.J., "The Application of Stable Isotopes in Biomedical Research", Biomedical Mass Spectrometry (1982), vol. 9:7, pp. 269-277.

Kushner et al., "Pharmacological uses and perspectives of heavy water and deuterated compounds," Can. J. Physiol. Pharmacal. (1999), vol. 77, pp. 79-88.

Park, et al. "Metabolism of Fluorine-Containing Drugs," Annu. Rev. Pharmacal. Toxicol. (2001), vol. 41, pp. 443-470.

Tang, G. et al., "Deuterium enrichment of retinol in humans determined by gas chromatography electron capture negative chemical ionization mass spectrometry", J. Nutr. Biochem (1998), vol. 9, pp. 408-414.

Tung, Office Action for U.S. Appl. No. 12/874,783, Dated Aug. 16, 2011.

Wolen, R., "The Application of Stable Isotopes to Studies of Drug Bioavailability and Bioequivalence", The Journal of Clinical Pharm. (1986), vol. 26, pp. 419-424.

Acutane [online], [retrieved on Jul. 5, 2012] Retrieved from RXlist: The Internet Drug Index using Internet <URL: http://www.rxlist.com/cgi/generic/isotret.htm>.

Age-Related Eye Disease Study Research Group, "A Randomized, Placebo-Controlled, Clinical Trial of High-Dose Supplementation with Vitamins C and E, Beta Carotene, and Zinc for Age-Related Macular Degeneration and Vision Loss," Arch. Ophthalmol. (2001) vol. 119, 1417-1436.

Alikmets, et al. "A photoreceptor cell-specific ATP-binding transporter gene (ABCR) is mutated in recessive Stargardt macular dystrophy," Nat. Genet (1997), vol. 15, pp. 236-246.

Ashmarin, et al. Thyroliberin: new physiological effects and prospects of clinical use, Vestn Ross Akad Med X Nauk (1992), vol. 6, pp. 40-44. (with abstract translation).

Baehr, et al. "The Retinoid Cycle and Retina Disease," Vision Research (2003) vol. 43, pp. 2957-2958.

Baillie, T., "The Use of Stable Isotopes in Pharmacological Research", Pharmacological Reviews(1981), vol. 33, No. 2, pp. 81-132.

Barrett, et al. "Hybrid Tracking System for Retinal Photocoagulation Prototype II," Biomed Sci Instrum (1999) vol. 35, pp. 259-264.

Bausch, et al. "Method for the Assessment of Vitamin A Liver Stores," Acta Vitaminol Enzymol31 (1977, ) pp. 99-112.

Ben-Shabat, et al. "Fluorescent pigments of the retinal pigment epithelium and age-related macular degeneration," Bioorg Med Chem Lett. 11(2001), pp. 1533-1540.

Bergen, et al. "Synthesis of Tri-, Tetra-, and Penta-Deuterated Forms of Vitamin A," Journal of Labelled compounds and Radiopharmaceuticals (1998), vol. 25:1, pp. 11-21.

Bergmann, et al. "Inhibition of the ATP-driven proton pump in RPE lysosomes by the major lipofuscin fluorophore A2-E may contribute to the pathogenesis of age-related macular degeneration," Faseb J.18 (2004), pp. 562-564.

Camerini, et al. "Safety of the Synthetic Retinoid Fenretinide: Long-Term Results From a Controlled Clinical Trial for the Prevention of Contralateral Breast Cancer," J. Clin. Oncol. (2001), vol. 19, pp. 1664-1670.

Capon, et al. "Sorsby's fundus dystrophy: a light and electron microscopic study," Ophthalmology 96 (1989), pp. 1769-1777.

Isotretinoin, [online], [retrieved on Jul. 5, 2012] Retrieved from Chemocare.com using Internet <URL: http://www.chemocare.com/bio/isotretinoin.asp>.

Chong, et al. TIMP-3 collagen, and elastin immunohistochemistry and histopathology of Sorsby's fundus dystrophy, Invest Ophthamol Vis Sci (2000), vol. 41, pp. 898-902.

De, et al. "Interaction of A2E with model membranes. Implications to the pathogenesis of age-related macular degeneration," J Gen Physiol. (2002), vol. 120, pp. 147-157.

Dowling, "Neural and Photochemical Mechanisms of Visual Adaptation in the Rat," J. Gen. Physio. (1963), pp. 1287-1301.

Dragnev, et al. "The Retinoids and Cancer Prevention Mechanisms," Oncologist 5 (2000), pp. 361-368.

Fine, et al. "Age-related macular degeneration," N Engl J Med. (2000), vol. 342, pp. 483-492.

Finnemann, et al. The lipofuscin component A2E selectively inhibits phagolysosomal degradation of photoreceptor phospholipid by the retinal pigment epithelium, Proc Natl Acad Sci. (2002), vol. 99, pp. 3842-3847.

Fishkin, et al. "Isolation and characterization of retinal pigment epithelial cell fluorophore: An all-trans-retinal dimer conjugate," Proc. Natl. Acad. Sci. (2005), vol. 102, pp. 7091-7096.

Freemantle, et al. "Retinoids in cancer therapy and chemoprevention: promise meets resistance," Oncogene (2003), vol. 22, pp. 7305-7315.

(56) References Cited

OTHER PUBLICATIONS

Friedman, et al. "Prevelance of age related macular degeneration in the United States," Arch. Ophthalmol. (2004) vol. 122, pp. 564-572.

Golczak, et al. "Metabolic Basis of Visual Cycle Inhibition by Retinoid and Non retinoid Compounds in the Vertebrate Retina," J. Biol. Chem. (2008), vol. 283, pp. 9543-9554.

Gollapalli, et al. The specific binding of retinoic acid to RPE65 and approaches to the treatment of macular degeneration, PNAS. (2004), vol. 101:27, pp. 10030-10035.

Gudas, et al. "Cellular biology and biochemistry of retinoids"; The retinoids, Biology, Chemistry and Medicine (1994), Raven Press Ltd., New York, pp. 443-520.

Haralampus-Grynaviski, et al. "Spectroscopic and morphological studies of human retinal lipofuscin granules," Proc. Natl. Acad. Sci. (2003), vol. 100, pp. 3179-3184.

Haskell, et al. "Use of deuterated-retinol-dilution technique to assess total body vitamin A stores of adult volunteers consuming different amounts of vitamin A1-3", Amer. J. of Clinical Nutrition (1999), vol. 70, pp. 874-880.

Jarc-Vidmar, et al. "Fundus autofluorescence imaging in Best's vitelliform dystrophy," Klinische Monatsblatter Fur Augenheilkunde (2003), vol. 220, pp. 861-867.

Jong, "Age-related macular degeneration," N. Engl J Med 355 (2006), pp. 1474-1485.

Katz, et al. "Relationship between dietary retinol and lipofuscin in the retinal pigment epithelium," Mech Age. Dev. (1986), vol. 35, pp. 291-305.

Kim, et al. "Rpe65 Leu450Met variant is associated with reduced levels of the retinal pigment epithelium lipofuscin fluorophores A2E and iso-A2E," Proc. Nat. Acad. Sci. (2004), vol. 101, pp. 11668-11672.

Maeda, et al. "Effects of potent inhibitors of the retinoid cycle on visual function and photoreceptor protection from light damage in mice," Mol. Pharmacal. (2006), vol. 70, pp. 1220-1229.

Maiti, et al. "Small molecule RPE65 antagonists limit the visual cycle and prevent lipofuscin formation," Biochemistry (2006), vol. 45, pp. 852-860.

Marmorstein, et al. "Spectral Profiling of Autofluorescence Associated with Lipofuscin, Bruch's Membrane, and Sub-RPE Deposits in Normal and AMD Eyes," Invest. Ophthalmol. Vis. Sci. (2002), vol. 43, pp. 2435-2441.

Murata, et al. "Suppression of laser-induced choroidal neovascularization by subconjunctival injection of 9alpha-fluoromedroxyprogesterone acetate (FMPA), an anti-angiogenic agent, in rats," Biol. Pharm Bull (2006), vol. 29:12, pp. 2410-2414.

Nason-Burchenal, et al. "The retinoids: cancer therapy and prevention mechanisms," Retinoids: The Biochemical and Molecular Basis of Vitamin A and Retinoid Action (1999), Berlin, pp. 301-322.

Owsley, et al. "Aging and scotopic dysfunction," Perception 29 (2000), Abstract Supplement.

Owsley, et al. "Delays in rod-mediated dark adaptation in early age-related maculopathy," Ophthalmology (2001), vol. 108, pp. 1196-1202.

Papadaki et al. "Somatostatin for Uveitic Cystoid Macular Edema (CME)," Ocul ImmunolInflamm (2005), vol. 13:6, pp. 469-470.

Pardoen, et al. "Synthesis of 8-, 9-, 12-, and 13-mono-13C-retinal," Canadian Journal of Chemistry (1985), vol. 63, pp. 1431-1435.

Pardoen, et al. "Synthesis of retina Is isotopically labeled at positions 11, 12, 14 and 20," Recueil des Travaux Chimiques des Pays-Bas (1986), vol. 105, pp. 92-98.

Halpern, et al. "Cystoid macular edema in aphakia and pseudophakia after use of prostaglandin analogs," Semin Ophthalmol (2002), vol. 17(3-4) pp. 181-186.

Puduvalli, et al. "Phase II Study of Fenretinide (NSC 374551) in Adults With Recurrent Malignant Gliomas: A North American Brain Tumor Consortium Study," J. Clin. Oncol. (2004), vol. 22, pp. 4282-4289.

Radu, et al. "Reductions in serum vitamin A arrest Accumulation of toxic retinal fluorophores: A potential therapy for treatment of lipofuscin based retinal diseases," Invest Ophthamol Vis Sci (2005), vol. 46, pp. 4393-4401.

Rattner, et al. "Macular degeneration: recent advances and therapeutic opportunities," Nat. Rev. Neurosci. (2006), vol. 7, pp. 860-872.

Radu, et al."Treatment with isotretinoin inhibits lipofuscin accumulation in a mouse model of recessive Stargardt's macular degeneration" Proc Natl Acad Sci (2003), vol. 100, pp. 4742-4747.

Radu, et al. "Light exposure stimulates formation of A2E oxiranes in a mouse model of Stargardt's macular degeneration," Proc Natl Acad Sci (2004), vol. 101, pp. 5928-5933.

Robison, et al. "Deficiencies of vitamins E and A in the rat. Retinal damage and lipofuscin accumulation," Invest Ophthamol Vis Sci (1980), vol. 19, pp. 1030-1037.

Saettel, et al. "Ab initio studies of [1 ,5]-H Shifts: pentadiene and beyond," J. Org. Chem. (2000), vol. 65, pp. 2331-2336.

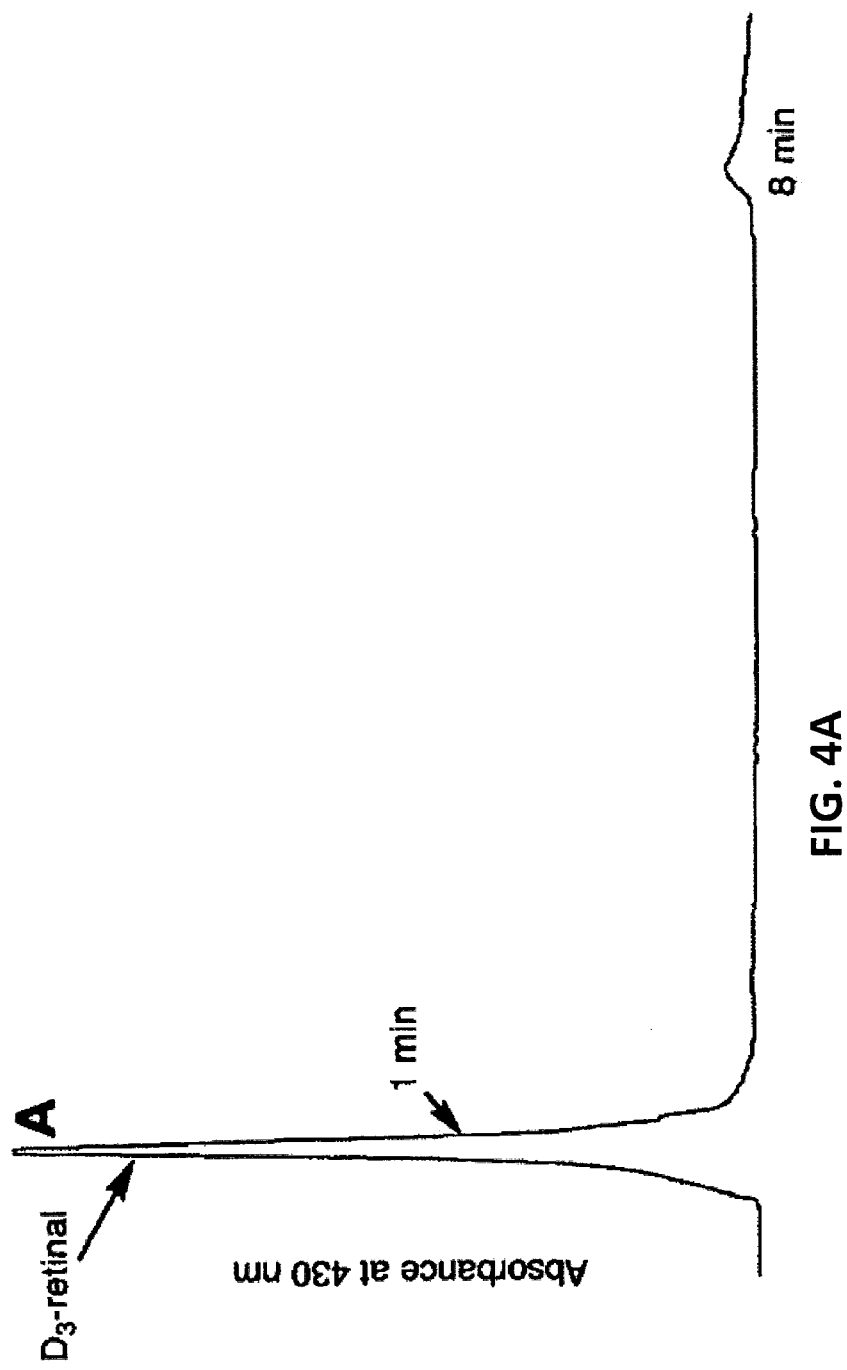

COMPOSITIONS AND METHODS FOR TREATING MACULAR DEGENERATION

CROSS-REFERENCE TO RELATED APPLICATIONS

The present application is a divisional of U.S. patent application Ser. No. 12/733,631, which is a U.S. National Stage Application of International Application No. PCT/US2008/010676, which was filed on Sep. 12, 2008, and claims the benefit of U.S. provisional patent application No. 60/993,379, filed 12 Sep. 2007, the disclosures of each of which are incorporated by reference as if recited in full herein.

FIELD OF THE INVENTION

The present invention relates, inter alia, to compounds, compositions, and methods to slow lipofuscin formation/accumulation in order to treat or ameliorate an ophthalmologic disorder, such as, e.g., macular degeneration, without, or with reduced, adverse visual effects. More particularly, the present invention relates to compounds and compositions that may be used to treat or ameliorate an ophthalmologic disorder, such as, e.g., macular degeneration, by slowing or limiting the accumulation of age pigments or lipofuscin in the retinal pigment epithelium ("RPE") cells of the retina. The present invention also relates to methods of treating or ameliorating an ophthalmologic disorder, such as, e.g., macular degeneration, in a mammal by administering to a mammal in need of such treatment an effective amount of the compounds and/or compositions disclosed herein.

BACKGROUND OF THE INVENTION

The macula is located at the back of the eye in the center of the retina. When the millions of cells in this light-sensitive, multilayer tissue deteriorate, central vision is lost along with the ability to perform tasks such as reading, writing, driving, and seeing color. This "macular degeneration" principally affects the elderly and has a prevalence of about 3% in populations between 75-79 years of age and about 12% for populations over 80 years of age.(1) In younger populations, macular degeneration is found in individuals with genetic disorders, such as Stargardt, Vitelliform or Best (VMD), Sorsby's Fundus Dystrophy and Malattia Leventinese (Doyne Honeycomb or Dominant Radial Drusen). Stargardt Disease is the most common form of inherited juvenile macular degeneration, affecting about 1 in 10,000 children.

There are no therapies currently available for genetic or dry (non-neovascular) age related macular degeneration. Vitamin supplements such as antioxidants, and diet changes, such as low fat diets, have been shown to slow disease progression in some clinical studies. However, for the majority of patients, diagnosis is followed by the progressive loss of central vision.(2-4)

The above listed macular dystrophies are all marked by the accumulation of lipofuscin, fluorescent deposits, in the retinal pigment epithelium (RPE) cell layer (5-11). The only compounds that have been characterized to date from RPE lipofuscin, A2E (N-retinylidene-N-retinylethanolamine) and ATR-dimer (all-trans-retinal dimer), are derived from reactions of all-trans-retinal, an isomer of 11-cis-retinal, the chromophore of the visual pigments (12, 13). These toxic retinal dimers have been shown to cause RPE cell death, which is thought to lead to photoreceptor cell degeneration and vision loss (2, 14-22). Slowing the visual cycle using RPE 65 antagonists (23-25) or retarding the delivery of vitamin A (retinol) to the RPE by, e.g., limiting dietary intake of vitamin A (26) or blocking serum retinol binding proteins (27) have been shown to impede or abolish RPE lipofuscin formation in animal models. Conversely, increasing the amount of all-trans-retinal in outer segments, such as occurs with the mutations in abcr$^{-/-}$ (responsible for recessive Stargardt disease), leads to the rapid accumulation of lipofuscin pigments (8).

The above cited evidence leads to the conclusion that lipofuscin and/or A2E and ATR-dimer in RPE cells may reach levels that contribute to a decline in cell function followed by vision loss and that vitamin A plays an important role in ocular lipofuscin formation. (28)

Several vitamin A analogs have been shown to limit lipofuscin formation in a mouse model by slowing down the visual cycle. The ABCR$^{-/-}$ mouse model has been used to test approaches to limit RPE lipofuscin formation. Mice lacking the ABCR (also known as ABCA4) gene encoding a photoreceptor-specific adenosine triphosphate (ATP)-binding cassette transporter, lack the ability to properly shuttle vitamin A (in the form of retinal) in the eye. ABCR$^{-/-}$ mice were developed as an animal model of human recessive Stargardt's Disease (8). As in humans with recessive Stargardt's disease, ABCR$^{-/-}$ mice accumulate large lipofuscin deposits in RPE cells of their eyes, as shown in FIG. 1, and eventually experience delayed dark adaptation. Lipofuscin accumulation and vision loss observed in this mouse model is also thought to be relevant to age-related macular degeneration (AMD) and other macular dystrophies.

In attempts to slow down the visual cycle, visual cycle enzymes have been targeted. In such approaches, small molecules have been proposed as antagonists to visual cycle enzymes. In this methodology, the drug (often a vitamin A derivative) binds to visual cycle proteins, which blocks participation by the proteins in the visual cycle, and slows the visual cycle. Another approach to slowing the visual cycle includes impeding the delivery of vitamin A from the blood to the eye.

Drug candidates for inhibiting lipofuscin formation by slowing down the visual cycle have been evaluated by their ability to cause delayed dark adaptation (a side effect of an impaired visual cycle) and their ability to impede the age related accumulation of eye lipofuscin as measured by the concentration of A2E and other byproducts of the visual cycle, e.g., ATR-dimer. Examples of such drug candidates and their corresponding mechanisms of action to slow the visual cycle are summarized below:

13 cis-retinoic acid (Acutane or isotretinoin) is thought to inhibit the enzymes 11-cis-retinol dehydrogenase and RPE65 involved in the visual cycle.(19, 24) When administered, 13 cis-retinoic acid has been shown to cause delayed dark adaptation. When 3-month-old ABCR knockout mice (n=3) were administered 13-cis-retinoic acid at 40 mg/kg/day for one month, the mice showed a decrease in A2E formation by about 40-50% compared to control ABCR knockout mice (n=3).(24) Furthermore, when 2-month-old ABCR knockout mice were administered 13-cis-retinoic acid at 20 mg/kg/day for two months, the mice also showed a decrease in lipofuscin formation in the RPE cell layer as judged by electron microscopy.

(12E,16E)-13,17,21-trimethyldocosa-12,16,20-trien-11-one (TDT) is thought to inhibit RPE65.(23) When TDT is administered to mice, delayed dark adaptation is observed. When 2-month-old ABCR knockout mice (n=2) were administered TDT at 50 mg/kg bi-weekly for two months, they showed a decrease in A2E formation by about 50-85% compared to control ABCR knockout mice (n=2).(23)

(2E,6E)-N-hexadecyl-3,7,11-trimethyldodeca-2,6,10-trienamine (TDH) is also thought to inhibit RPE65 and when given to mice, causes delayed dark adaptation.(23) When 2-month-old ABCR knockout mice (n=2) were administered TDH at 50 mg/kg bi-weekly for two months, they showed a decrease in A2E formation by about 50% compared to control ABCR knockout mice (n=2).(23)

All-trans-retinylamine (Ret-NH$_2$) is thought to inhibit RPE65 and when administered to mice results in severe delayed dark adaptation. When 1-month-old ABCA4 knockout mice were given Ret-NH$_2$ at 40 mg/kg bi-weekly for two months, they showed a decrease in A2E formation by about 50% compared to control ABCA4 knockout mice.(25)

N-(4-hydroxyphenyl) retinamide (Fenretinide) slows the influx of retinol into the eyes by reducing levels of vitamin A bound to serum retinol-binding protein. Thus, treatment with Fenretinide lowers the levels of vitamin A in the eye which leads to delayed dark adaptation. When 2-month-old ABCA4 knockout mice (n=3) were administered Fenretinide at 20 mg/kg/day for one month, they showed a decrease in A2E formation by about 40-50% compared to control ABCA4 knockout mice (n=3).(27)

Thus, recently proposed therapeutic approaches to limit lipofuscin formation are based upon slowing the visual cycle (1, 10, 11, 12). There are, however, disadvantages to slowing the visual cycle as a means to impede lipofuscin formation in order to prevent, e.g., macular degeneration. Four of these disadvantages are detailed below.

One immediate disadvantage of slowing the visual cycle is that it leads to delayed dark adaptation and poor vision in dim light or at night. Poor night vision (Scotopic dysfunction) is already a functional marker of early age-related maculopathy (ARM), and has been linked to the occurrence of falls and vehicle collisions.(29, 30) A further slowing down of the visual cycle is expected to make night vision worse in patients who already suffer from poor night vision.

Second, in order to sufficiently impede lipofuscin formation, one would have to slow down the visual cycle for a prolonged period of time. But, long-term slowing of the visual cycle leads to photoreceptor cell death and loss of vision.(31, 32) In fact, impairment of the visual cycle is the cause of various retinal diseases such as Stargardt's disease, retinitis pigmentosa, Lebers Congenital Amaurosis, Fundus Aibipunctatus, age-related macular degeneration and Congenital Stationary Night Blindness.

Third, the above methodology often uses vitamin A analogs to impede proteins involved in vitamin A processing in the eye. However, vitamin A analogs of diverse structures, pharmacological profiles, receptor affinities, and biologic activities have been shown to be toxic. Indeed, numerous vitamin A analogs have been shown in experimental animal models, cellular models, epidemiological data and clinical trials to inhibit or retard various biological functions such as, for example, bone growth, reproduction, cell division, cell differentiation and regulation of the immune system.(33-37). Thus, inhibiting vitamin A processing in the eye is also expected to retard some of these basic bodily functions, which may lead to significant adverse side effects.

For example, vitamin A analogs that are currently used to treat certain cancers and/or psoriasis such as, e.g., Bexarotene (Targretin), Etretinate (Tegison) Acitretin (Soriatane), Fenretinide (N-(4-hydroxyphenyl) retinamide or 4-HPR) and 13 cis-retinoic acid (Accutane or isotretinoin) have side effects, which include, e.g., dry nose, nosebleeds, chapped lips, mouth sores, increased thirst, sore tongue, bleeding gums, dry mouth, cold sores, dry or irritated eyes, dry skin, peeling or scaly skin, hair loss, easy bruising, muscle aches, nausea, stomach upset, cough or swelling of the hands or feet, vision problems, chest pain, tightness in the chest, abnormal pulse, dizziness, vomiting, severe headache, and yellowing of the eyes/skin (jaundice).(38-40)

Fourth, in animal models, candidate drugs for limiting lipofuscin formation have been shown to be effective only in relatively large doses. For example, studies in mouse models typically use doses around 11-40 mg/kg/day. But, current vitamin A analogs are typically used in the clinic at doses of 1-3 mg/kg/day to minimize side effects. Larger dosing regimes will lead to increased side effects.

For example, Fenretinide (N-(4-hydroxyphenyl) retinamide or 4-HPR) is currently used to treat cancer and clinical trails are in progress for AMD. The most common adverse effects reported among 1,432 patients who underwent treatment with this drug at a dosage of 200 mg/day for a five year period were: diminished dark adaptation, cumulative incidence (16%) and dermatologic disorders (16%). Less common effects were gastrointestinal symptoms (8%) and disorders of the ocular surface (8%).(41) At this relatively low dose a delay in dark adaptation, an assessment of the effectiveness of a drug to impede lipofuscin formation, was only observed in 16% of patients. In another study when patients were administered larger oral doses of 600 or 900 mg/m$^2$ bid in 6-week cycles, mild to moderate adverse effects were reported in 43 (95%) of the 45 patients that were possibly linked to Fenretinide. These side effects included: fatigue, headache, skin changes (dry skin, pruritus, and rash) and digestive tract symptoms (abdominal pain, cramping, diarrhea, stomatitis, and xerostomia). Grade 2 toxicities reported as possibly linked to Fenretinide treatment included seizures and confusion.(42)

A patient with an anaplastic astrocytoma who had been receiving treatment with Fenretinide at the 600 mg/m$^2$ bid dose for one cycle presented with headaches, nausea, and vomiting, and was found to have a small intracranial bleed in the region of the basal ganglia. He recovered without deficits and continued treatment without further events. Another patient, who was also undergoing treatment at the 600 mg/m$^2$ bid dosage and was receiving oral anticoagulation with warfarin for deep venous thrombosis, died after developing an uncontrollable nasal bleed (international normalized ratio>6.0). Of the four patients treated at the 900 mg/m$^2$ bid dose, one had grade 3 vomiting, grade 2 speech impairment, and grade 1 memory impairment, which improved without residual symptoms.(42)

A typical dose of 13 cis-retinoic acid (Accutane or isotretinoin) for treatment of acne is 0.5 to 1 mg/kg/day for children and 2.0 mg/kg/day for adults for fourteen days in a row, followed by a 14-day break. This twenty-eight day course is usually repeated five more times.(40) These doses are about 10 to 80 times less than what was used in mice to impede A2E formation.(24) For larger doses of 13 cis-retinoic acid used to treat cancer, side effects occurring in more than 30% of users included headache, fever, dry skin, dry mucous membranes (mouth, nose), bone pain, nausea and vomiting, rash, mouth sores, itching, sweating, and eyesight changes.(43, 44)

Side effects occurring in 10-29% of users of 13 cis-retinoic acid include back pain, muscle and joint pain, allergic reaction, abdominal pain, poor appetite, dizziness, drowsiness, insomnia, anxiety, numbness and tingling of hands and feet, weakness, depression, hair loss (thinning), dry eyes, sensitivity to light (see eye problems), decreased night vision, which may persist after treatment is stopped, feet or ankle swelling, and low blood counts.(44) In addition, it has been observed that white and red blood cells and platelets may temporarily decrease, which may put a patient at increased risk for infection, anemia and/or bleeding. Side effects also include abnormal blood tests: increased triglyceride, cholesterol and/or blood sugar levels.

The above disadvantages make slowing of the visual cycle a difficult methodology to adapt alone for the clinical treatment of ophthalmologic disorders, e.g., macular degeneration.

SUMMARY OF THE INVENTION

Accordingly, it would be advantageous to provide treatments for ophthalmologic disorders, e.g., macular degeneration, that do not have, or limit one or more of, the side effects summarized above. In particular, it would be advantageous to provide compounds, compositions, and methods for impeding or halting the accumulation of lipofuscin or age pigments in the RPE cells of the retina without slowing, or slowing minimally, the visual cycle.

In this regard, one embodiment of the present invention is a method of retarding formation of a lipofuscin pigment in the retina. This method includes the step of administering to a patient in need thereof a substituted $C_{20}$-retinoid in an amount sufficient to reduce accumulation of a lipofuscin pigment in the retina.

Another embodiment of the present invention is method of treating or ameliorating the effects of a disease characterized by an accumulation of a lipofuscin pigment in a retina. This method includes the step of administering to a patient in need thereof a substituted $C_{20}$-retinoid in an amount sufficient to reduce accumulation of a lipofuscin pigment in the retina.

A further embodiment of the present invention is a method of retarding formation of A2E. This method includes the step of replacing an all-trans-retinal (ATR) substrate with a $C_{20}$-$D_3$-retinoid substrate in a patient under conditions sufficient to impede the formation of A2E.

An additional embodiment of the present invention is a composition for retarding formation of a lipofuscin pigment in the retina containing a substituted $C_{20}$-retinoid and pharmaceutically acceptable carrier.

A further embodiment of the invention is a composition comprising a pharmaceutically acceptable carrier and a compound according to formula I:

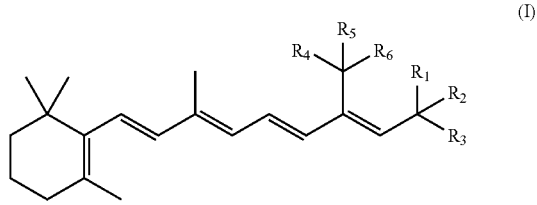

(I)

wherein:
  $R_1$ is oxo or H;
  $R_2$ is H or nothing;
  $R_3$ is hydroxy or oxo or $CHR_7$ where $R_7$ forms a carotenoid and
  $R_4$, $R_5$, and $R_6$ are independently selected from the group consisting of $^1H$, $^2H$, $^3H$, halogen, and $C_{1-8}$alkyl.

BRIEF DESCRIPTION OF THE DRAWINGS

FIGS. 4A and 4B shows HPLC profiles of reaction mixtures of $C_{20}$-$D_3$-all-trans-retinal (FIG. 4A) and all-trans-retinal (FIG. 4B) with proline for the formation of ATR-dimer. ATR-dimer formation was monitored over time by measuring the appearance of peaks starting at around 8 min. Both HPLC traces were measured about 1 hour into the reactions. For all-trans-retinal, a considerable amount of ATR-dimer has formed. On the other hand, for $C_{20}$-$D_3$-all-trans-retinal ATR-dimer formation is much slower.

DETAILED DESCRIPTION OF THE INVENTION

In the present invention, methods are provided to slow lipofuscin formation that do not rely on slowing the visual cycle or small molecules that inhibit the visual cycle (i.e., visual cycle antagonists). Thus, many of the disadvantages, such as, delayed dark adaptation, unformed visual pigment, which can leading to vision impairment and loss, high drug doses, and the potentially adverse side effects of prior methods are avoided.

More particularly, in the present invention provides methods for selectively replacing atoms on vitamin A in order to hamper its intrinsic reactivity to form vitamin A derived lipofuscin pigments, such as, A2E and ATR dimer, while at the same time preserving the chemical structure of vitamin A such that participation in the visual cycle (binding to visual cycle proteins) is minimally disturbed. Because such changes to the structure of vitamin A do not interfere with normal vitamin A metabolism or function, one of the utilities of the present invention is that many potential side effects are avoided. Furthermore, because the compounds of the present invention (disclosed in more detail below) do not compete with natural retinoids for protein binding (because, e.g., they can perform the job of natural retinoids), smaller doses are needed for treatment of e.g., macular degeneration, compared to previous treatments using, e.g., visual cycle antagonists.

Figure 1:
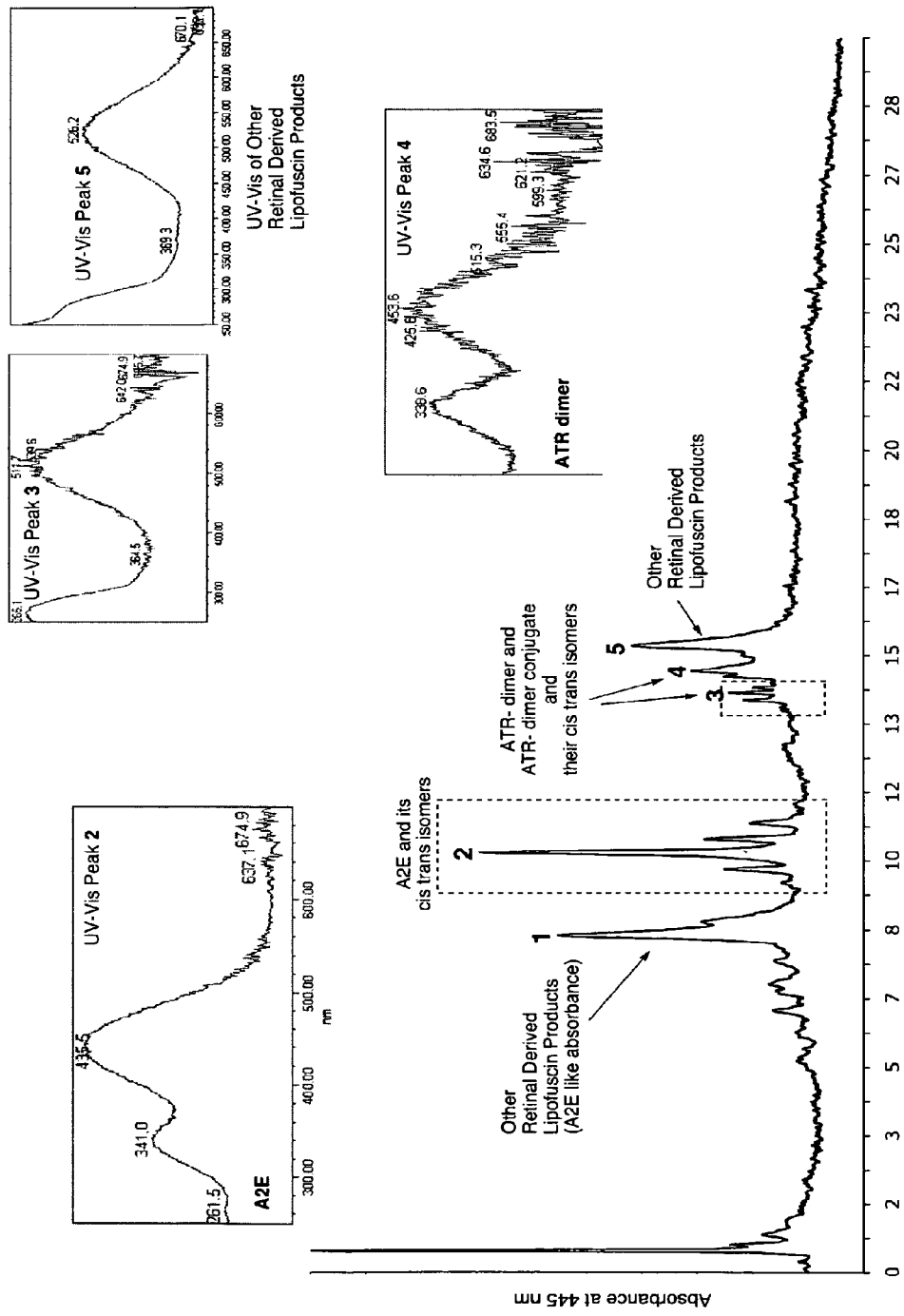
FIG. 1 shows HPLC and UV-vis profiles of lipofuscin pigments extracted from the eyecups (six of them minus the retina) of 5.5-6 month old, $ABCR^{-/-}$ mice. Lipofuscin pigments such A2E and ATR dimer, represented by peaks 2, 3 and 4 have been characterized and are derived from all-trans-retinal. Other lipofuscin pigments such as peaks 1 and 5 are also derived from all-trans-retinal, however, they have not been fully characterized. The above pigments are also found in humans and are thought to contribute to the macular degeneration.
Figure 2:
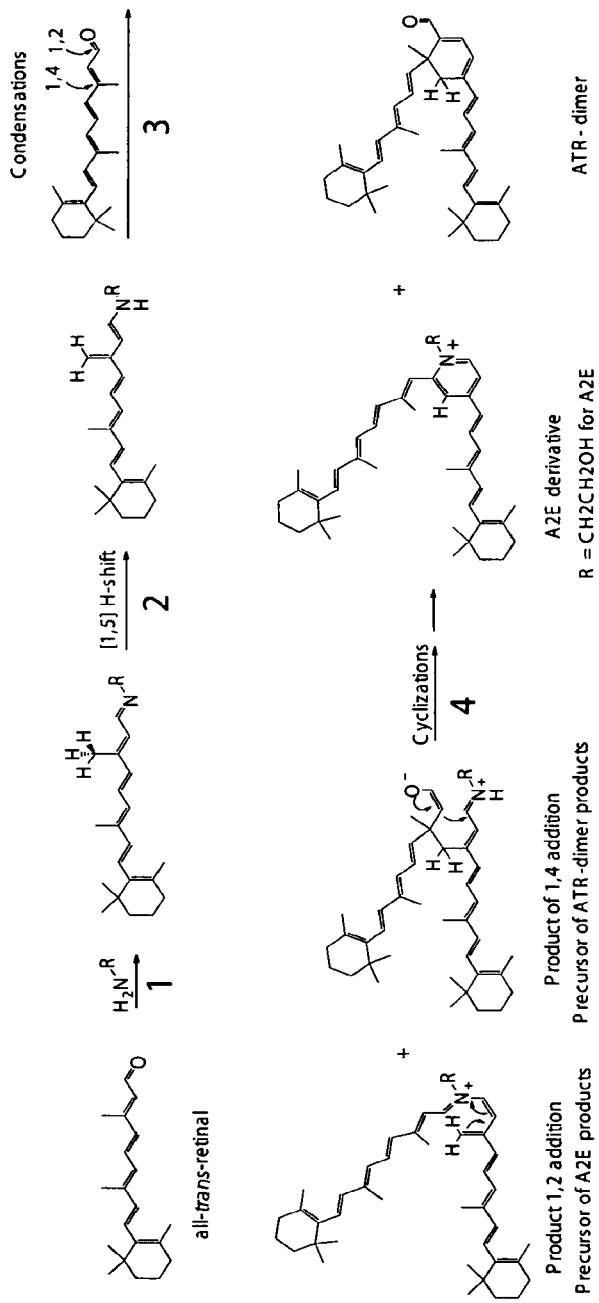
FIG. 2 is a reaction scheme showing the biosynthesis of A2E and ATR-dimer from all-trans-retinal and a biological amine.

In the present invention, when the $C_{20}$ hydrogens of all-trans-retinoids are replaced by fluorine atoms ($F_3$), the formation of A2E is eliminated, as measured by monitoring the disappearance of $C_{20}$—$F_3$-all-trans-retinal and the absence of the corresponding fluorinated A2E by HPLC. A2E and the ATR-dimer are believed to be formed in vivo by a multi-step reaction sequence involving two molecules of all-trans-retinal, as shown in FIG. 2. In the first step, all-trans-retinal condenses with a biological amine to form the imine. This imine is then thought to undergo a [1,5] hydrogen shift involving a hydrogen atom at carbon $C_{20}$ (step 2). Subsequent reaction (step 3) with another molecule of retinal either by 1,2- or 1,4-addition followed by cyclizations (step 4) yields A2E or ATR-dimer precursors, respectively. A2E is subsequently formed after spontaneous oxidation in air, and ATR dimer, after elimination (step 4).

It has been shown that replacing certain C—H bonds with C—F bonds in retinal (i.e., $C_{20}$—$F_{1-3}$-retinal) hampers the reactivity of all-trans-retinal, and, thus slows or eliminates the formation of A2E in vitro. By replacing hydrogen atoms at $C_{20}$ with fluorine, the [1,5] hydrogen shift step is blocked. Accordingly, $C_{20}$—$F_{1-3}$-retinal is expected to appreciably slow A2E and ATR-dimer biosynthesis.

A small change in the reaction rate of all-trans-retinal to form its toxic dimers is expected to translate into a large decrease in RPE lipofuscin formation over a lifetime. The methods of the present invention will slow the formation of the toxic pigments and will not slow (or will not slow significantly) visual cycle kinetics, because the regeneration of 11-cis-retinal does not involve the breaking of the $C_{20}$ hydrogen bond. Therefore, treatment with a $C_{20}$—$F_{1-3}$-retinoid (which may be transformed into $C_{20}$—$F_{1-3}$-retinal in the body) will be particularly useful in impeding lipofuscin formation in humans who suffer from Stargardt Disease or other diseases or conditions associated with lipofuscin formation and/or macular degenerations.

$C_{20}$-$D_{1-3}$-retinoid according to the present invention will also be useful as a therapy to treat or ameliorate macular degeneration without adverse (or significantly adverse) visual effects. When $C_{20}$ hydrogens are replaced by deuteriums, A2E formation is about seven times slower (FIG. 3) and ATR-dimer formation is about 15 times slower (FIG. 4). This kinetic isotope effect will slow A2E and ATR-dimer formation in vivo. Deuterated vitamin A is widely used in humans and shows no toxicity (45, 46). Thus, a treatment using a $C_{20}$-$D_{1-3}$-retinoid should be an effective and non-toxic therapy to treat or ameliorate macular degeneration without adverse visual effects.

In view of the foregoing, one embodiment of the present invention is a method of retarding formation of a lipofuscin pigment in the retina. This method includes the step of administering to a patient in need thereof a substituted $C_{20}$-retinoid in an amount sufficient to reduce accumulation of a lipofuscin pigment in the retina. Preferably, the substituted $C_{20}$-retinoid is selected from the group consisting of a $C_{20}$-$D_{1-3}$-retinoid and a $C_{20}$—$F_{1-3}$-retinoid. Preferably, the lipofuscin pigment is selected from the group consisting of A2E, all-trans-retinoid (ATR)-dimer, and combinations thereof.

Preferably, the substituted $C_{20}$-retinoid is administered to the patient as part of a pharmaceutical or a nutraceutical composition. Preferably, the substituted $C_{20}$-retinoid is administered as a unit dosage form.

In the present invention, the patient may be a mammal, preferably a human. In this embodiment, the substituted $C_{20}$-retinoid is a compound or combination of compounds disclosed herein, preferably compounds of Formula I, including Formulae Ic-Ie and Formula II, which are defined below.

In this embodiment, an amount sufficient to reduce accumulation of a lipofuscin pigment in the retina will vary by patient and the particular substituted $C_{20}$-retinoid used. Typically, such amount will be about 0.05 to about 300 mg/day, including, e.g., 0.5-50, 1-25, and 3-10 mg/day.

Another embodiment of the present invention is method of treating or ameliorating the effects of an ophthalmologic disorder, such as, e.g. a disease characterized by an accumulation of a lipofuscin pigment in a retina. This method includes the step of administering to a patient in need thereof a substituted $C_{20}$-retinoid in an amount sufficient to reduce accumulation of a lipofuscin pigment in the retina. Preferably, the substituted $C_{20}$-retinoid is selected from the group consisting of $C_{20}$-$D_{1-3}$-retinoids and $C_{20}$—$F_{1-3}$-retinoids. Preferably, the lipofuscin pigment is selected from the group consisting of A2E, ATR-dimer, and combinations thereof.

Preferably, the substituted $C_{20}$-retinoid is administered as part of a pharmaceutical or a nutraceutical composition. Preferably, the substituted $C_{20}$-retinoid is administered as a unit dosage form.

In this embodiment, the disease maybe selected from the group consisting of Stargardt, Vitelliform or Best (VMD), Sorsby's Fundus Dystrophy, age related macular degeneration, and Malattia Leventinese. Preferably, the disease is macular degeneration.

In this embodiment, the administration step includes replacing a component of the patient's diet that contains retinoid(s) or Vitamin A with a component that contains a substituted $C_{20}$-retinoid. By "replacing a component of a patient's diet" it is meant that a part of the diet that contains vitamin A or its precursors (including, but not limited to carotenoids) is replaced with a component that contains a substituted $C_{20}$-retinoid. Preferably, from about 1% to about 95%, including, e.g., from about 5-75%, 10-50%, or 20-30%, of the retinoid(s) in the patient's diet is replaced with a substituted $C_{20}$-retinoid. The replacement may be through, e.g., administering substituted $C_{20}$-retinoid containing foods or through treatment with compositions of the present invention, including pharmaceuticals or nutraceuticals, in lieu of consuming retinoid- or Vitamin A-containing foods that would have otherwise been consumed.

An additional embodiment of the present invention is a composition for retarding formation of a lipofuscin pigment in the retina, which composition contains a substituted $C_{20}$-retinoid and a pharmaceutically acceptable carrier. Preferably, the substituted $C_{20}$-retinoid is selected from the group consisting of $C_{20}$-$D_{1-3}$-retinoid and $C_{20}$—$F_{1-3}$-retinoid. Preferably, the composition is in a unit dosage form. Preferably, the composition is a vitamin supplement or a pharmaceutical formulation.

A further embodiment of the present invention is a method of retarding formation of a lipofuscin pigment selected from the group consisting of an A2E, an ATR dimer, and combinations thereof. This method comprises replacing an all-trans-retinal (ATR) substrate with a $C_{20}$-$D_3$-retinoid substrate under conditions sufficient to impede the formation of A2E, ATR dimer, or both, or an A2E and/or an ATR-dimer derivative. As used in the present invention, "conditions sufficient to impede the formation of A2E, ATR dimer, or both are well known in the art or may be determined empirically, if desired. The replacing step in this embodiment is described in more detail below.

A further embodiment of the present invention is a method of retarding formation of A2E. This method includes the step of replacing an all-trans-retinal (ATR) substrate with a $C_{20}$-$D_3$-retinoid substrate under conditions sufficient to impede the formation of A2E. The replacing step in the last two embodiments may be accomplished using known method, including the methods disclosed above. For example, the substrate replacement may take place in the eye of the patient, e.g., the substrate may be administered directly to the eye via eye drops, ointment, or injection. Alternatively, the substrate may be administered systemically via, e.g., ingestion of a pill or capsule or absorption through a patch or by injection.

In the present invention, the "substituted $C_{20}$-retinoid" includes all retinols, retinol acetates, retinol esters, and retinoic acids as defined below as well as pharmaceutical salts thereof and metabolites thereof. For purposes of the present invention, the number scheme set forth in formula Ia for retinoids shall be used:

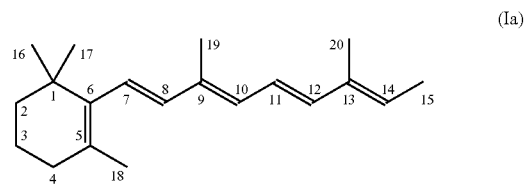 [SMILES: C/C=C(C)/C=C/C=C(C)/C=C/C1=C(C)CCCC1(C)C]

(Ia)

Thus, retinol, retinol acetate, retinol palmitate, retinoic acid, and beta-carotene have the following structures:

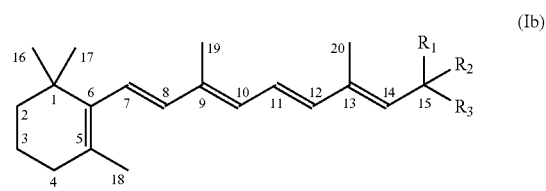

(Ib)

wherein $R_1$ and $R_2$ are both H and $R_3$ is OH (retinol); or $R_1$ and $R_2$ are both H and $R_3$ is $OCOCH_3$ (retinol acetate); or $R_1$ and $R_2$ are both H and $R_3$ is OCOR (retinol ester such as, e.g., retinol palmitate) or $R_1$ is =O, $R_2$ is nothing and $R_3$ is OH (retinoic acid) or $R_1$ is H, $R_3$ is nothing, and $R_2$ is =CH—$R_7$, where $R_7$ forms a carotenoid. In this embodiment, $R_7$ together with the rest of the compound forms, e.g., a beta-carotene or another pro-vitamin A carotenoid such as the deuterated beta-carotene shown in formulae Ib' below:

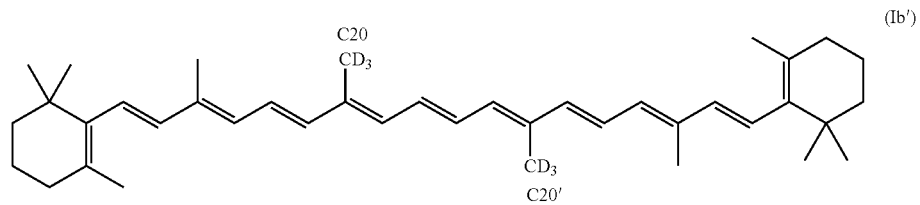

(Ib')

Exemplary substituted $C_{20}$-retinoid compounds that may be used in the compositions of the present invention include the following (compounds Ic-Ie):

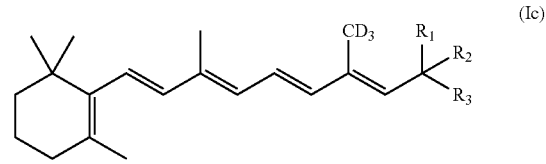

(Ic)

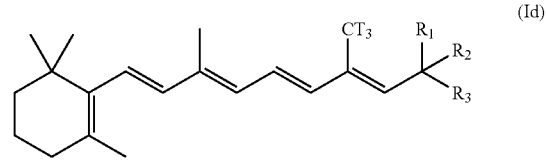

(Id)

-continued

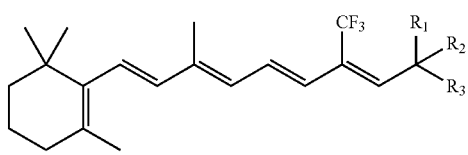

wherein $R_1$, $R_2$, and $R_3$ are as defined in Formula Ib.

Exemplary methods and reaction schemes for making substituted C20-retinoid compounds according to the present invention are set forth below:

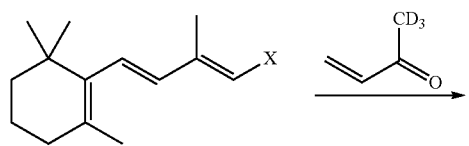

X = halogen

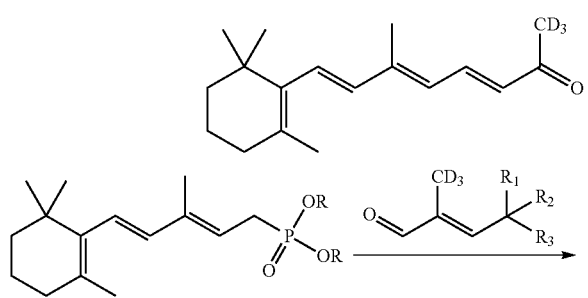

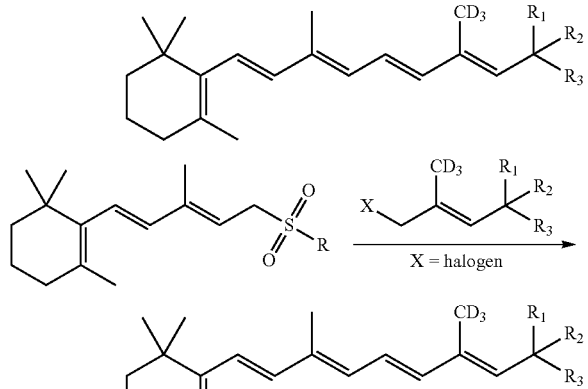

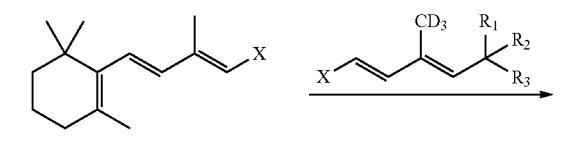

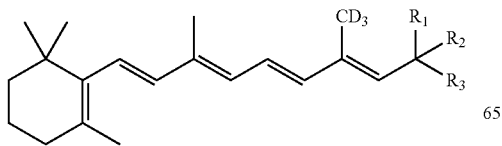

X = halogen, SnR$_3$ (where r = alkyl), B(OH)$_2$, OTf

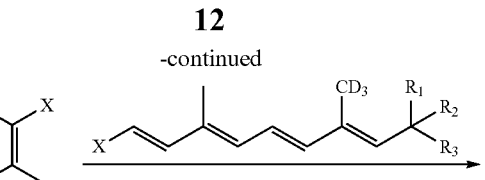

X = halogen,
SnR$_3$
(where r = alkyl),
B(OH)$_2$, OTf

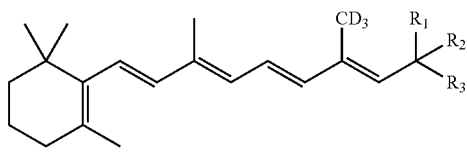

In another embodiment, the invention is a composition comprising a pharmaceutically acceptable carrier and a compound according to formula I:

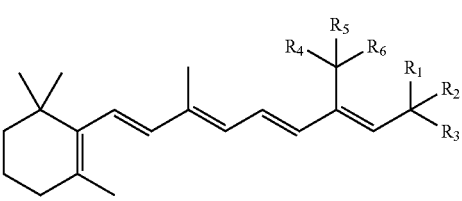

wherein:
$R_1$ is oxo or H;
$R_2$ is H or nothing;
$R_3$ is hydroxy or oxo or =CH—$R_7$, where $R_7$ forms a carotenoid; and
$R_4$, $R_5$, and $R_6$ are independently selected from the group consisting of $^2$H (D), $^3$H (T), halogen, and $C_{1-8}$alkyl. Preferably, the halogen is fluorine (F).

In this embodiment, $R_4$, $R_5$, and $R_6$ may also be independently selected from H or a substituent that slows lipofuscin formation, a substituent that slows the formation of at least one of A2E or ATR dimer formation, or a substituent that slows hydrogen abstraction or migration at the $C_{20}$ position compared to a retinoid that is not substituted at the $C_{20}$ position, e.g. a $C_{20}$—$H_3$ retinoid. The present invention further contemplates any combination of the foregoing substituents at $R_4$, $R_5$, and $R_6$.

Preferably, in the composition of the present invention the compound has the structure of formula II:

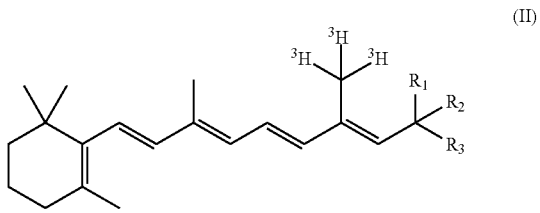

wherein:
$R_1$ is oxo or H;
$R_2$ is H or nothing; and
$R_3$ is hydroxy or oxo or =CH—$R_7$, where $R_7$ forms a carotenoid.

In the present invention, the compositions may further contain a supplement. Representative, non-limiting examples of a supplement according to the present invention are visual cycle antagonists, molecules that inhibit influx of a retinoid into an eye, or combinations thereof.

Exemplary, non-limiting visual cycle antagonists according to the present invention include TDH, TDT, 13-cis-retinoic acid, ret-NH$_2$, and combinations thereof. An exemplary, non-limiting visual cycle antagonist according to the present invention is fenretinide. Other visual cycle antagonists within the scope of the present invention include those disclosed in R. Rando, U.S. application Ser. No. 11/199,594 filed Aug. 8, 2005, which application is incorporated by reference as if recited in full herein.

In the present invention, one or more additives may be included in the compositions. Exemplary, non-limiting additives that may be included in the compositions of the present invention include zinc, vitamin E, vitamin D, and combinations thereof.

The zinc, vitamin E, and vitamin D additives may be present in the compositions of the present invention in amounts that are effective to, e.g., enhance the bioavailability of the substituted $C_{20}$-retinoid compounds of the present invention, including Formula I, Formulae Ic-e, and Formula II. Thus, in the present invention, zinc may be present in the composition at between about 3 to about 80 mg, preferably between about 3 to about 10 mg or between about 10 to about 80 mg. Vitamin E may be present in the composition at between about 3 to about 3,000 mg, preferably between about 3 to about 15 mg or between about 15 to about 3,000 mg. Vitamin D may be present in the composition at between about 0.005 to about 0.1 mg, preferably between about 0.005 to about 0.015 mg or between about 0.015 to about 0.1 mg.

The compositions of the present invention may also include one or more additional additives, including, for example, eye antioxidants, minerals, negatively-charged phospholipids, carotenoids, and combinations thereof. The use of anti-oxidants has been shown to benefit patients with macular degenerations and dystrophies. See, e.g., Arch. Ophthalmol., 119: 1417-36 (2001); Sparrow, et al., J. Biol. Chem., 278:18207-13 (2003). Examples of suitable anti-oxidants that could be used in a composition of the present invention in combination with a compound of formulae I, including formulae Ic-Ie and II, include vitamin C, vitamin E, beta-carotene and other carotenoids, coenzyme Q, OT-551 (Othera Pharmaceuticals Inc.), 4-hydroxy-2,2,6,6-tetramethylpiperidine-N-oxyl (also known as Tempol), butylated hydroxytoluene, resveratrol, a trolox analogue (PNU-83836-E), bilberry extract, and combinations thereof.

The use of certain minerals has also been shown to benefit patients with macular degenerations and dystrophies. See, e.g., Arch. Ophthalmol., 119: 1417-36 (2001). Thus, the present invention contemplates the optional inclusion of one or more of such minerals. Examples of suitable minerals that could be used in a composition of the present invention include copper-containing minerals, such as cupric oxide (by way of example only); zinc-containing minerals, such as zinc oxide (by way of example only); and selenium-containing compounds, and combinations thereof.

The use of certain negatively-charged phospholipids has also been shown to benefit patients with macular degenerations and dystrophies. See, e.g., Shaban & Richter, Biol. Chem., 383:537-45 (2002); Shaban, et al., Exp. Eye Res., 75:99-108 (2002). Examples of suitable negatively charged phospholipids that could optionally be used in a composition of the present invention include cardiolipin, phosphatidylglycerol, and combinations thereof. Positively-charged and/or neutral phospholipids may also provide benefit for patients with macular degenerations and dystrophies when used in combination with a composition of the present invention.

The use of certain carotenoids has been correlated with the maintenance of photoprotection necessary in photoreceptor cells. Carotenoids are naturally-occurring yellow to red pigments of the terpenoid group that can be found in plants, algae, bacteria, and certain animals, such as birds and shellfish. Carotenoids are a large class of molecules in which more than 600 naturally occurring carotenoids have been identified. Carotenoids include hydrocarbons (carotenes) and their oxygenated, alcoholic derivatives (xanthophylls). They include actinioerythrol, astaxanthin, canthaxanthin, capsanthin, capsorubin, beta-8'-apo-carotenal (apo-carotenal), beta-12'-apo-carotenal, alpha-carotene, beta-carotene, "carotene" (a mixture of alpha- and beta-carotenes), gamma-carotenes, beta-cyrptoxanthin, lutein, lycopene, violerythrin, zeaxanthin, and esters of hydroxyl- or carboxyl-containing members thereof. Many of the carotenoids occur in nature as cis- and trans-isomeric forms, while synthetic compounds are frequently racemic mixtures.

In humans, the retina selectively accumulates mainly two carotenoids: zeaxanthin and lutein. These two carotenoids are thought to aid in protecting the retina because they are powerful antioxidants and absorb blue light. Examples of suitable carotenoids for optional use in a composition of the present invention include lutein and zeaxanthin, as well as any of the aforementioned carotenoids and combinations thereof.

Effective dosage forms, modes of administration, and dosage amounts, in addition to those disclosed above, may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of a compound according to the invention will be that amount of the compound, which is the lowest dose effective to produce the desired effect. For example, a compound of the invention is present in the composition at a level sufficient to deliver about 0.1 to about 90 mg/day to a patient. The effective dose of a compound maybe administered as two, three, four, five, six or more sub-doses, administered separately at appropriate intervals throughout the day.

A compound of the present invention may be administered in any desired and effective manner: as pharmaceutical compositions for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, a compound of the present invention may be administered in conjunction with other treatments. A compound or composition of the present invention maybe encapsulated or otherwise protected against gastric or other secretions, if desired.

While it is possible for a compound of the invention to be administered alone, it is preferable to administer the compound as a pharmaceutical formulation (composition) or a vitamin supplement or a nutraceutical. The pharmaceutically acceptable compositions of the invention comprise one or more compounds as an active ingredient in admixture with one or more pharmaceutically-acceptable carriers and, optionally, one or more other compounds, drugs, ingredients and/or materials. Regardless of the route of administration selected, the compounds of the present invention are formulated into pharmaceutically-acceptable dosage forms by conventional methods known to those of skill in the art. See, e.g., Remington's Pharmaceutical Sciences (Mack Publishing Co., Easton, Pa.).

Pharmaceutically acceptable carriers are well known in the art (see, e.g., Remington's Pharmaceutical Sciences (Mack Publishing Co., Easton, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable carrier used in a pharmaceutical composition of the invention must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

The pharmaceutical compositions or vitamin supplements or nutraceuticals of the invention may, optionally, contain additional ingredients and/or materials commonly used in such pharmaceutical compositions or vitamin supplements or nutraceuticals. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monosterate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Pharmaceutical compositions or vitamin supplements or nutraceuticals suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared by mixing the active ingredient(s) with one or more pharmaceutically-acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type maybe employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Pharmaceutical compositions for rectal or vaginal administration may be presented as a suppository, which maybe prepared by mixing one or more active ingredient(s) with one or more suitable nonirritating carriers which are solid at room temperature, but liquid at body temperature and, therefore, will melt in the rectum or vaginal cavity and release the active compound. Pharmaceutical compositions which are suitable for vaginal administration also include pessaries, tampons, creams, gels, pastes, foams or spray formulations containing such pharmaceutically-acceptable carriers as are known in the art to be appropriate.

Dosage forms for the topical or transdermal administration include powders, sprays, ointments, pastes, creams, lotions, gels, solutions, patches, drops and inhalants. The active compound may be mixed under sterile conditions with a suitable pharmaceutically-acceptable carrier. The ointments, pastes, creams and gels may contain excipients. Powders and sprays may contain excipients and propellants.

Pharmaceutical compositions suitable for parenteral administrations comprise one or more compound in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation or vitamin supplement or nutraceutical), it is desirable to slow its absorption from subcutaneous or intramuscular injection. This may be accomplished by the use of a liquid suspension of crystalline or amorphous material having poor water solubility.

The rate of absorption of the drug then depends upon its rate of dissolution which, in turn, may depend upon crystal size and crystalline form. Alternatively, delayed absorption of a parenterally-administered drug may be accomplished by dissolving or suspending the drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

The following examples are provided to further illustrate the methods of the present invention. These examples are illustrative only and are not intended to limit the scope of the invention in any way.

EXAMPLES

Example 1

Replacing the $C_{20}$ Hydrogens of all-Trans-Retinal with Deuteriums Slows the Formation of A2E In Vitro $C_{20}$-$D_3$-retinal was prepared according to the literature procedure(47) and its in vitro ability to form A2E as compared to all-trans-retinal was measured by HPLC.

Figure 3A:
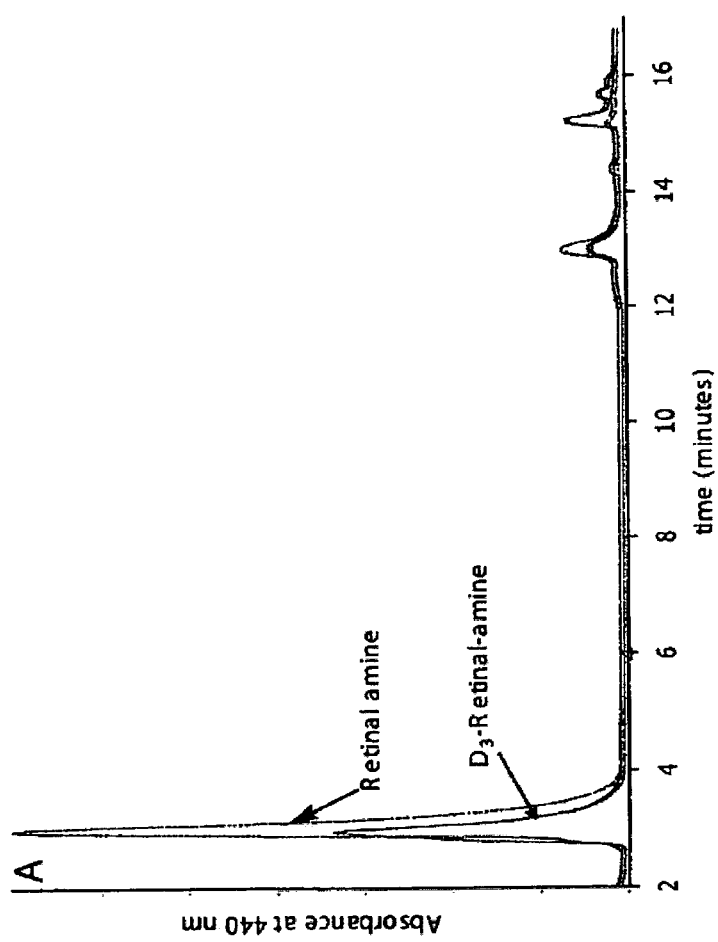
FIG. 3A shows HPLC profiles of reaction mixtures of $C_{20}$-$D_3$-all-trans-retinal and all-trans-retinal with ethanolamine for the formation of A2E.
Figure 3B:
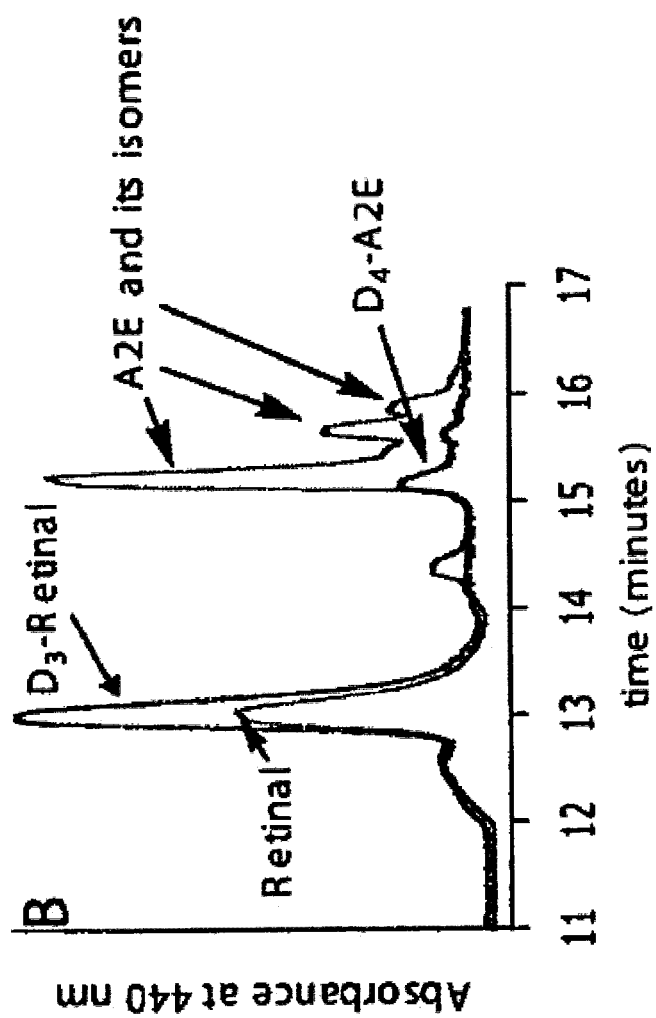
FIG. 3B is an expanded view of FIG. 3A. A2E formation was monitored over time by measuring the appearance of peaks starting at around 15 min. Both HPLC traces were measured about 30 hours into the reactions. For all-trans-retinal, a considerable amount of A2E has formed as well as an unidentified compound with a retention time at around 14.5 min as seen in the expanded view. On the other hand, for $C_{20}$-$D_3$-all-trans-retinal A2E formation is much slower and the peak at 14.5 min is almost absent.
Figure 3C:
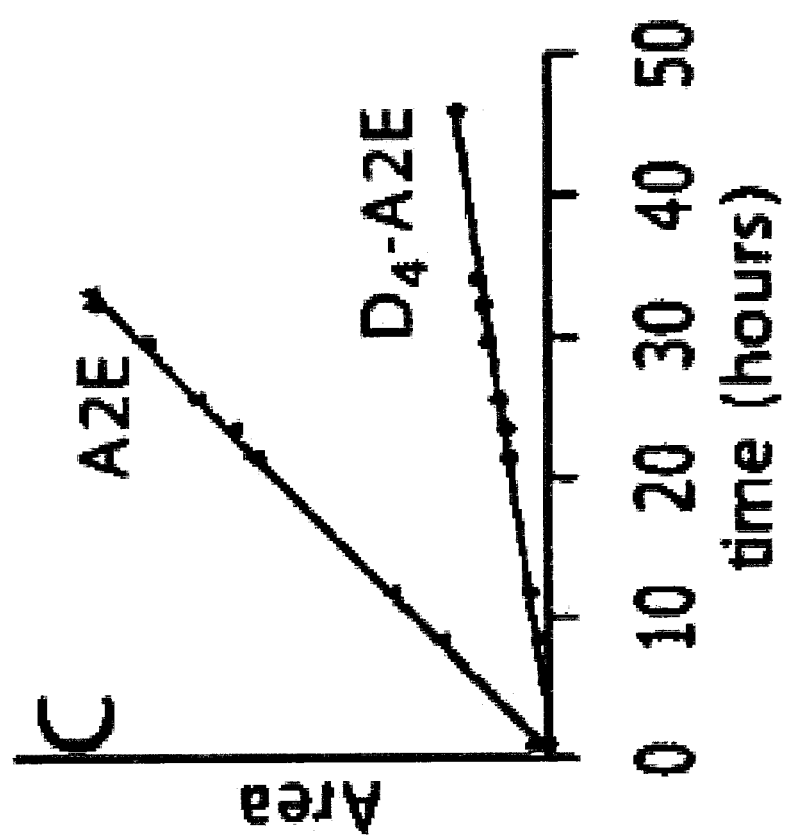
FIG. 3C is a plot of A2E formation over time for the above reactions. $C_{20}$-$D_3$-all-trans-retinal forms A2E about 7-times slower than all-trans-retinal.

FIG. 3A plots the formation of all A2E for two reaction mixtures containing either all-trans-retinal or $C_{20}$-$D_3$-all-trans-retinal (16 mg), ethanolamine (0.5 equivalents) and acetic acid (1.2 equivalents). A typical HPLC trace is shown in FIG. 3B for the all-trans-retinal and $C_{20}$-$D_3$-all-trans-retinal reaction mixtures. The area under the curve corresponds to the amount of A2E: the larger the area the more A2E. The concentrations of A2E in the two reactions mixtures were measured about every 8 hours for 50 hours. The concentrations at each time point was plotted and the data points fit to a line for each reaction mixture. A comparison of the slopes of the two lines for the two reaction revealed that A2E formation occurred 7-times faster for all-trans-retinal compared to $C_{20}$-$D_3$-all-trans-retinal. Hydrogen deuterium exchange was not observed during the reaction with the labeled retinal, as measured by mass spectrometry of the reaction mixture after 50 hours, which clearly showed the presence of the tri-deuterated retinal, tri-deuterated retinal hydroxylamine Schiff base and tetra-deuterated A2E.

Example 2

Figure 4B:
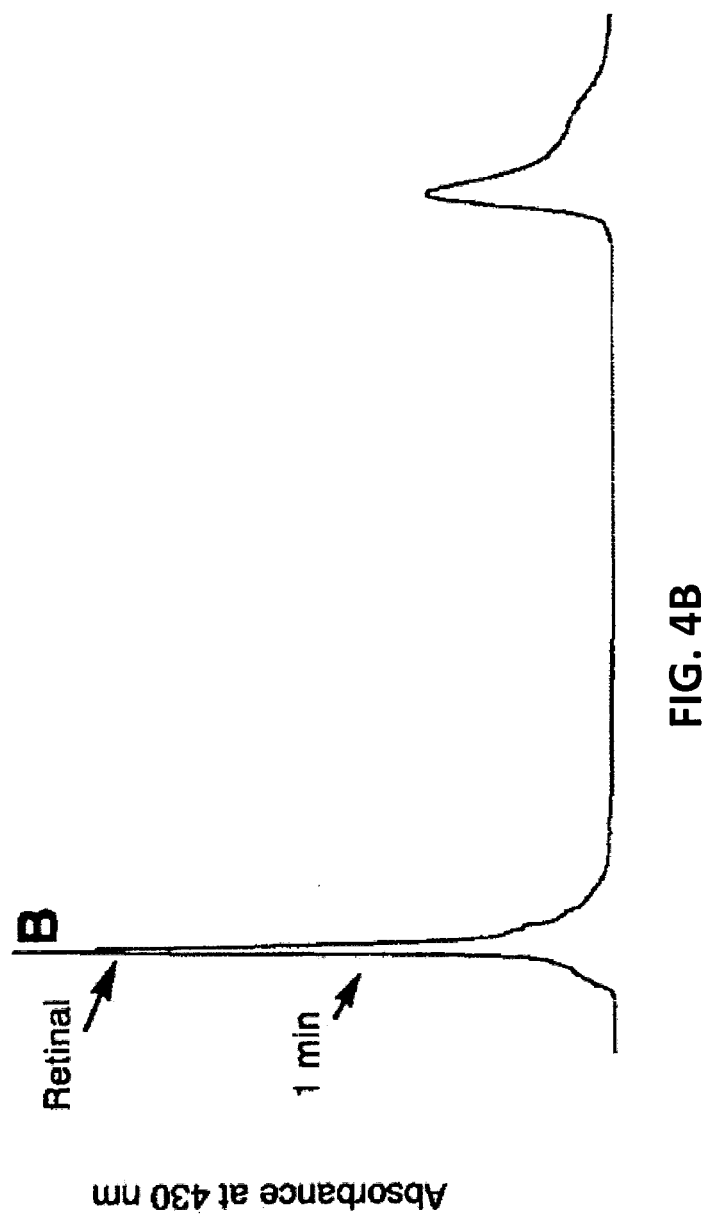
Figure 4C:
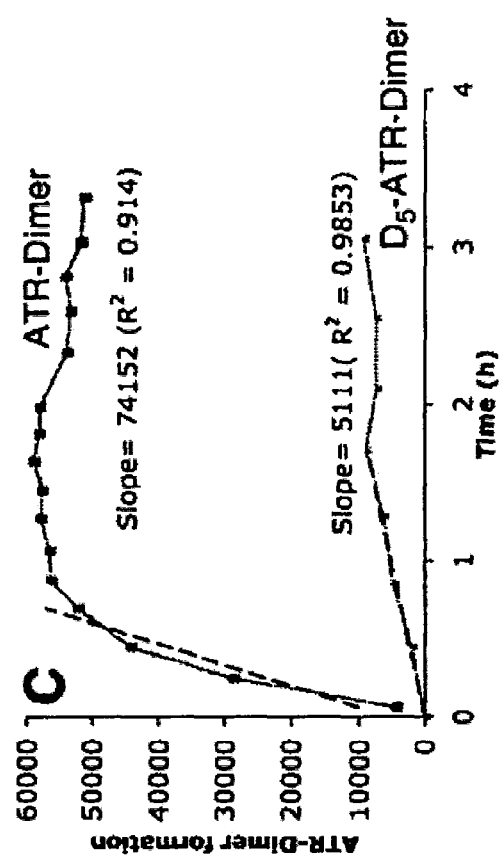
FIG. 4C is a plot of ATR-dimer formation over time for the above reactions. $C_{20}$-$D_3$-all-trans-retinal forms A2E about 14-times slower than all-trans-retinal.

Replacing the $C_{20}$ Hydrogens of all-Trans-Retinal with Deuteriums Slows the Formation of ATR-Dimer In Vitro $C_{20}$-$D_3$-all-trans-retinal was prepared as described in Example 1 and its in vitro ability to form ATR-dimer as compared to all-trans-retinal was measured by HPLC. All-trans-retinal or $C_{20}$-$D_3$-all-trans-retinal (10 mg) and proline (2 equivalents) in ethanol were mixed, and the reaction was followed by HPLC, the results of which are depicted in FIG. 4A. A typical HPLC trace is shown in FIG. 4B for the all-trans-retinal and $C_{20}$-$D_3$-all-trans-retinal reaction mixtures at the same time points. The concentrations of ATR-dimer in the two reaction mixtures were measured about every 15 min for 3 hours. The concentration at each time point was plotted and the data points fit to a line for each reaction mixture. A comparison of the slopes of the two lines showed that $C_{20}$-$D_3$-all-trans-retinal formed ATR-dimer 15 times slower than the unlabeled retinal as shown in FIG. 4C.

Example 3

Replacing the $C_{20}$ Hydrogens of all-Trans-Retinal with Deuteriums Slows the Formation of A2E-Lipofuscin in CD-1 (ICR) Mice $C_{20}$-$D_3$-all-trans-retinal was administered to mice in order to measure its ability to form A2E in the eye compared to all-trans-retinal. Nine, 8-week old, CD-1 (ICR) mice (from Charles River, Wilmington, Mass.) were divided up into two groups of five and administered 1.5 mg of ether all-trans-retinal or $C_{20}$-$D_3$-all-trans-retinal by intraperitoneal injection (IP) injection in a 10% solution of Tween-20 in saline bi-weekly for 6 weeks. At the end of this six-week period, each mouse was given a total of 60,000 I.U. (18 mg) or about 28-times the original amount of vitamin A in the mouse's body. Massive dosing with $C_{20}$-$D_3$-all-trans-retinal quickly replaces normal vitamin A stores with the $C_{20}$-$D_3$-analog. And, the injected retinal rapidly accumulates in the eye (rod outer segments), where at high enough concentrations it will react to form lipofuscin pigments. This is similar to the accumulation of all-trans-retinal in the ABCR$^{-/-}$ mice and in patents with Stargardt's disease.

At the end of the six week period, the eyes were dissected, the retinas and eyecups pooled into groups of 4 or 5, and homogenated with 50 µL ethanol. The homogenate was centrifuged at 13,000 rpm for 5 minutes and 40 µL of the supernatant was drawn off and analyzed for A2E-lipofuscin by HPLC. Retinol and retinol esters were analyzed at 325 nm and A2E-lipofuscin was measured at 445 nm. Mice administered $C_{20}$-$D_3$-all-trans-retinal (n=5) had 68% less A2E-lipofuscin as compared to mice administered all-trans-retinal (n=4). Both groups of mice had roughly the same concentrations of retinol and retinol esters.

Example 4

Replacing the $C_{20}$ Hydrogens of all-Trans-Retinal with Deuteriums Reduces the Formation of A2E in ABCR$^{-/-}$ Mice $C_{20}$-$D_3$-all-trans-retinol acetate was prepared according to the literature procedure(47) and was administered to ABCR$^{-/-}$ mice (48, 49) in order to measure its ability to lead to lipofuscin compared to that of all-trans-retinol acetate. Eight 2-month old, ABCR$^{-/-}$ mice raised on a standard rodent diet were then fed a diet containing 20,000 I.U./kg of either $C_{20}$-$D_3$-all-trans-retinol acetate or all-trans-retinol acetate for 3 months. On this diet each mouse roughly received the daily-recommended amount of vitamin A or the same amount of the $C_{20}$-$D_3$-vitamin A drug, which was less than about 1 mg/kg/day.

At the end of the 5 month period, the eyes were dissected, eyecups pooled into groups of six and homogenated with 80 µL ethanol. The homogenate was centrifuged at 13000 rpm for 5 min and 30 µL of the supernatant was drawn off and analyzed for A2E-lipofuscin by HPLC. A2E-lipofuscin was measured at 445 nm. Mice on the 3-month diet containing $C_{20}$-$D_3$-all-trans-retinol acetate had 44-58% less A2E-lipofuscin as compared to mice on a diet of all-trans-retinol acetate. This percentage of A2E reduction is on the same order of magnitude observed in similar studies in ABCR$^{-/-}$ mice with the visual cycle antagonist TDH, TDT, Ret-NH$_2$, 13-cis-retinoic, acid and fenretinide. However, in this example A2E reduction is achieved with doses of $C_{20}$-$D_3$-all-trans-retinol acetate that are 11- to 40-times less.

Example 5

Figure 5A:
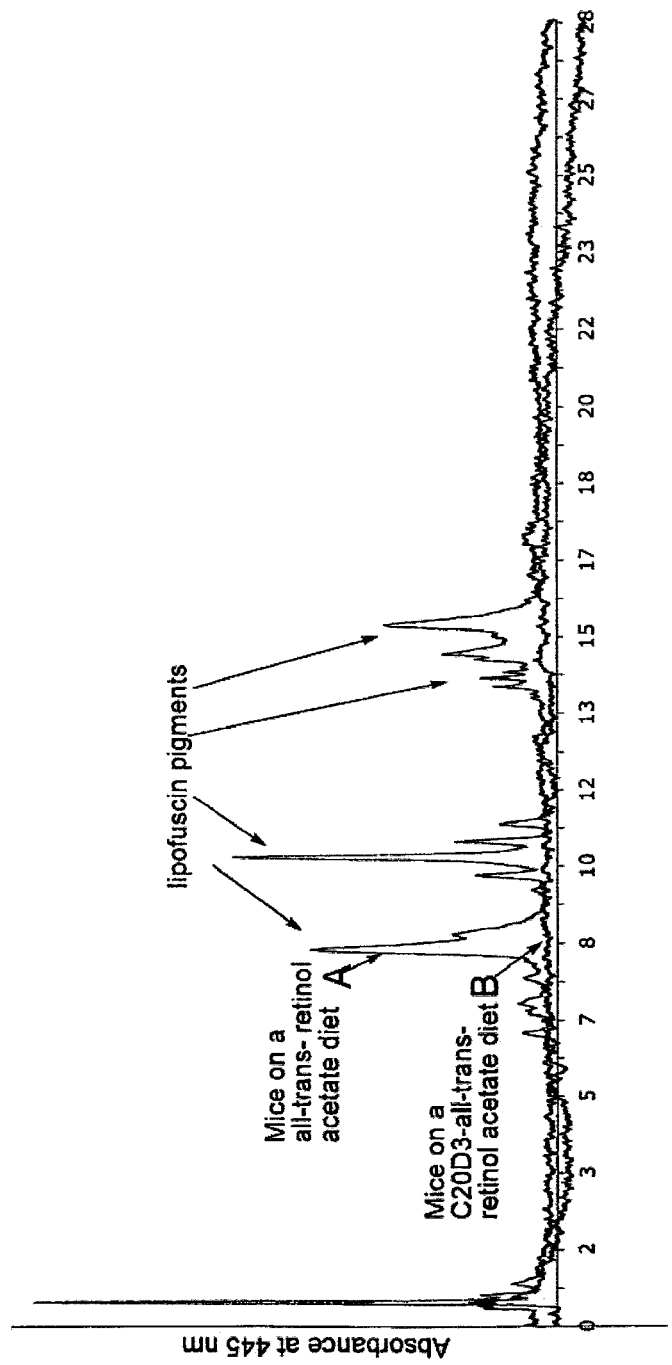
FIG. 5A shows HPLC profiles of lipofuscin pigments extracted from the eyecups (six of them minus the retina) of 5.5-6 month old, $ABCR^{-/-}$ mice raised on a diet of either retinol acetate (trace A (FIG. 5A)) or $C_{20}$-$D_3$-all-trans-retinol acetate (trace B (FIG. 5A)). Mice raised on retinol acetate show considerable accumulation of lipofuscin pigments as shown by the HPLC peaks. On the other hand, lipofuscin pigments were undetectable in mice raised on the $C_{20}$-$D_3$-all-trans-retinol acetate diet.
Figure 5B:
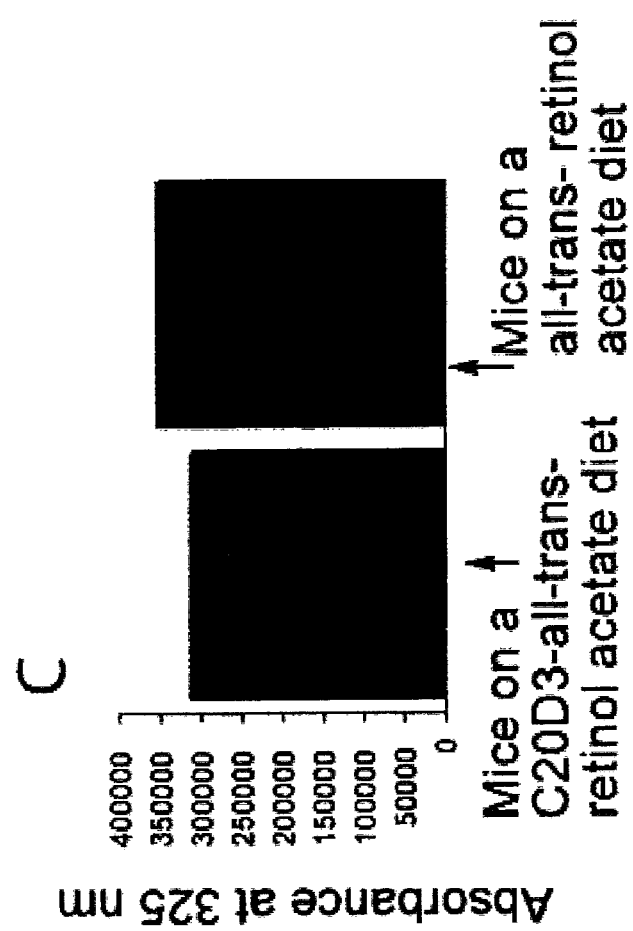
FIG. 5B shows plots of total retinol and retinol ester or $D_3$-retinol and $D_3$-retinol ester concentrations in the above mice raised on either the retinol acetate or $C_{20}$-$D_3$-all-trans-retinol acetate diets, respectively. Both groups had roughly the same amount of retinol in the eye, despite having different concentrations of lipofuscin pigments.

ABCR$^{-/-}$ Mice Raised Exclusively on a $C_{20}$-$D_3$-all-Trans-Retinol Acetate Diet Show Undetectable Amounts of Extractable Lipofuscin Pigments and Reduced Lipofuscin Deposits As in Example 4, two groups of four ABCR$^{-/-}$ mice where raised either on diets containing $C_{20}$-$D_3$-all-trans-retinol acetate or all-trans-retinol acetate. However, in this example the mice were offspring of mothers on the same diet, and thus where raised only on their respective vitamin A analogs. At 5.5-6 months of age the mice were sacrificed and the eyecups were analyzed for lipofuscin pigments as described in Example 4. The results are shown FIG. 5. While both mice contained the same amount of eye retinol and retinol esters (FIG. 5B) lipofuscin pigments were undetectable in mice raised on the $C_{20}$-$D_3$-all-trans-retinol acetate diet (FIG. 5A) but were detectable in mice raised on the all-trans-retinol acetate diet (FIG. 5A).

Figures 6A, 6B:
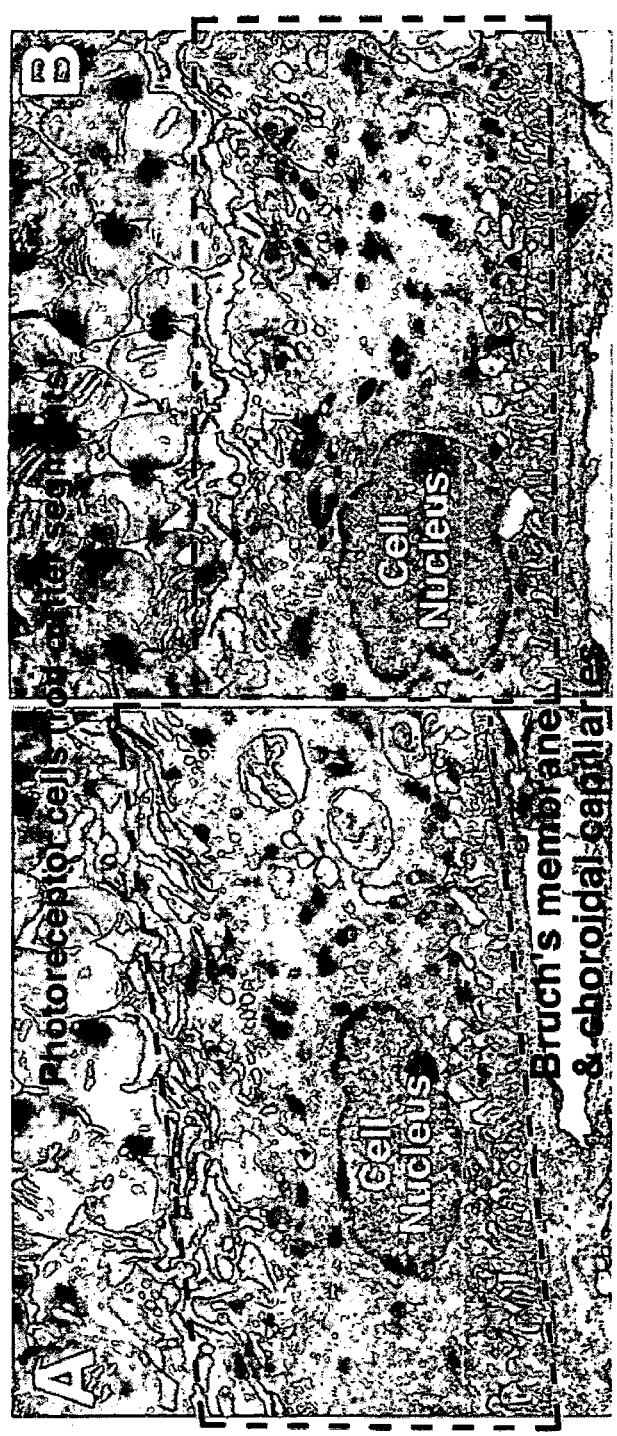
FIG. 6A-D shows electron micrographs of RPE layers from 5.5-6 month old, $ABCR^{-/-}$ mice raised on a diet of either retinol acetate (FIGS. 6A and 6B) or $C_{20}$-$D_3$-all-trans-retinol acetate (FIGS. 6C and 6D). Due to the uncertainty in distinguishing lipofuscin from melanin bodies. Comparisons were made between the numbers of all dark, electron dense bodies found in the RPE between mice on the retinol acetate diet vs. those on the $C_{20}$-$D_3$-all-trans-retinol acetate diet. In addition to the electron dense lipofuscin and melanin bodies, RPE phagosomes, mitochondria, and lipid droplets are also present but were ultrastructurally distinct. Mice raised on the $C_{20}$-$D_3$-all-trans-retinol acetate diet have considerably less electron dense bodies (i.e. lipofuscin bodies) compared to mice raised on the retinol acetate diet.
Figures 6C, 6D:
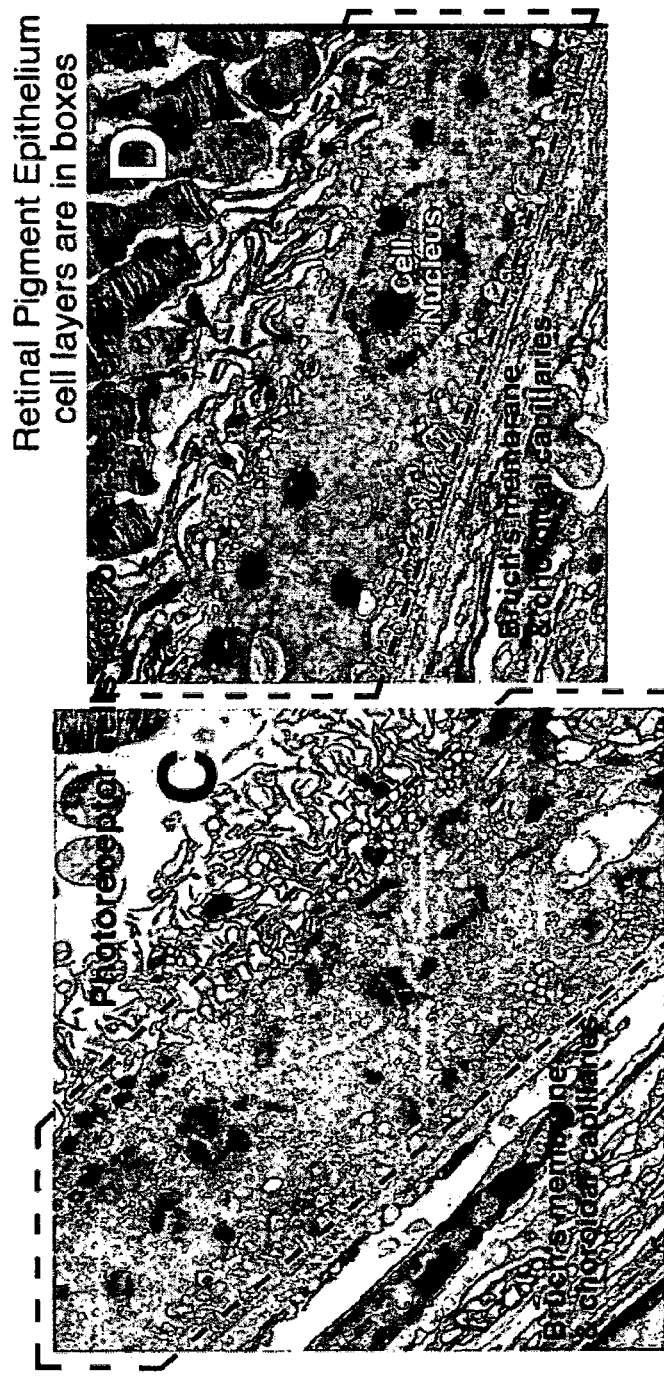

In order to measure the amount lipofuscin granules in the eyes of the above mice on a normal diet vs. the diet containing C20D$_3$-all-trans-retinol acetate, eyecups from both groups of mice (2 from each group) were evaluated by electron microscopy. Mice on the $C_{20}$-$D_3$-all-trans-retinol acetate diet had less electron dense lipofuscin deposits compared to mice on a diet of all-trans-retinol acetate as shown in FIG. 6.

Example 6

$C_{20}$-$D_3$-all-Trans-Retinal Slows A2E-Lipofuscin Formation as Well as Fenretinide and/or TDH in Wild-Type Rats 45-50 day old, female, CD IGS rats (Charles River, Wilmington, Mass.) were divided up into four groups of three. Three of these groups were administered all-trans-retinal and the one group was given $C_{20}$-$D_3$-all-trans-retinal (IP injection in a 10% solution of Tween-20 in saline) at 3 mg, bi- or tri-weekly for 8 weeks (20, 3 mg injections total). Thus, at the end of the 8-week period the animals received roughly 20 times their original stores of vitamin A, as retinal or $C_{20}$-$D_3$-all-trans-retinal. Massive dosing with $C_{20}$-$D_3$-all-trans-retinal quickly replaces normal vitamin A stores with the $C_{20}$-$D_3$-analog. Of the three groups administered all-trans-retinal, one group was given Fenretinide (50) and another TDH (23), at doses of roughly 1.5 mg/day/animal (both supplied in the drinking water emulsified with 1 g/L of Nu-rice (RIBUS, Inc, St. Louis, Mo.)).

Figure 7A:
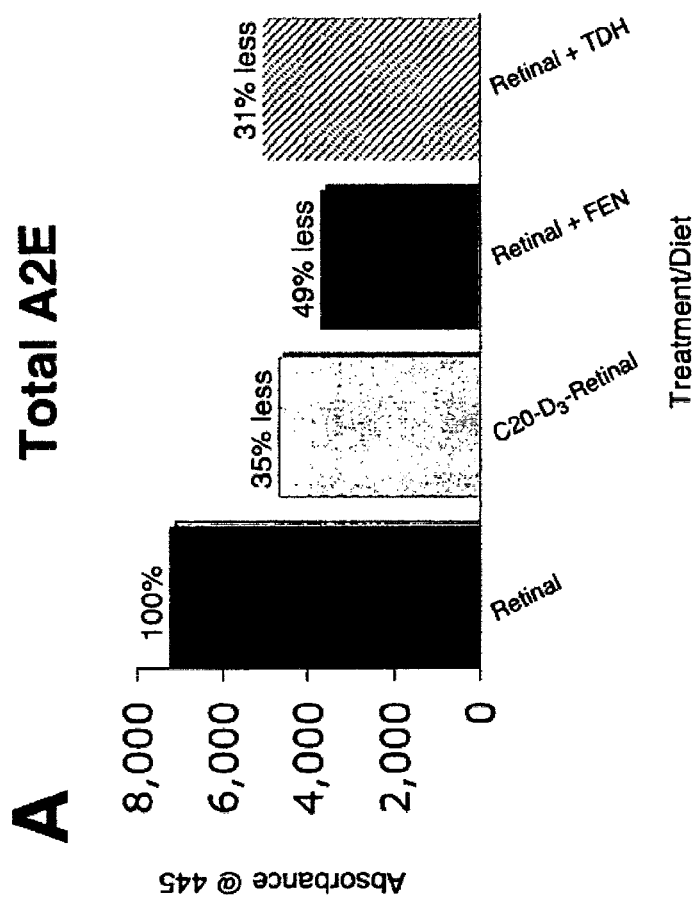
FIG. 7A shows total A2E, as measured by HPLC peak area at 445 nm, for rats (three females per group) treated/raised on either retinal, $C_{20}$-$D_3$-retinal, retinal plus Fenretinide (FEN) or retinal plus TDH. Animals treated with retinal had the greatest amount of A2E-lipofuscin (normalized to 100%). Whereas, animals treated with $C_{20}$-$D_3$-retinal or retinal plus Fenretinide or the RPE65 antagonist, TDH, showed less A2E-lipofuscin.
Figure 7B:
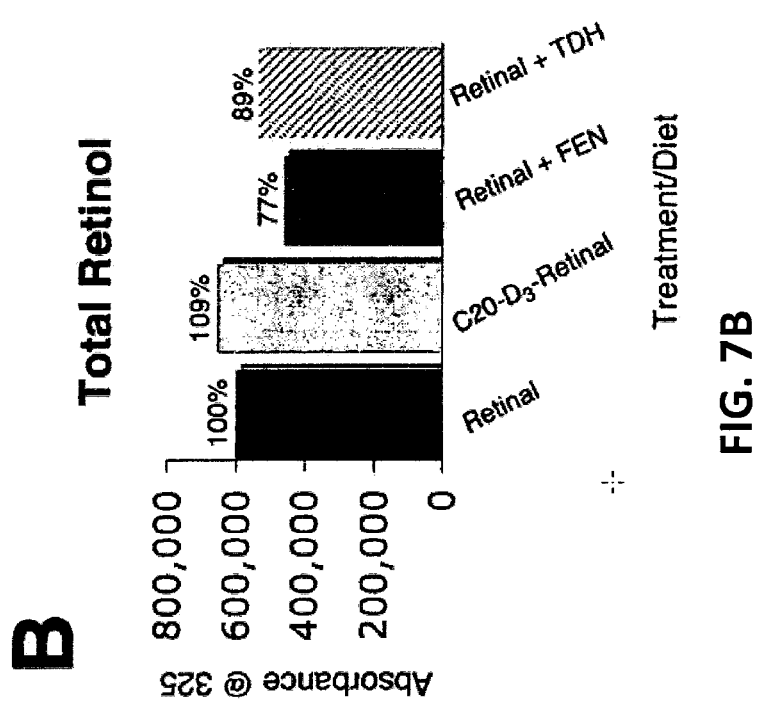
FIG. 7B shows that all four groups of animals had roughly the same amount of eye retinal.
Figure 7C:
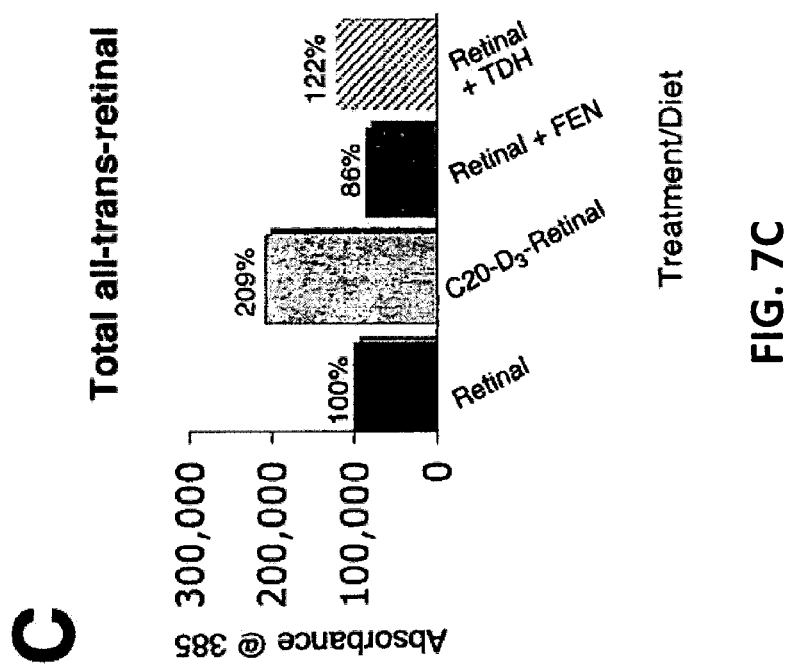
FIG. 7C shows that levels of eye all-trans-retinal were increased in the $C_{20}$-$D_3$-retinal group.

At the end of the 8 weeks, RPE, A2E-lipofuscin was evaluated in each of the four groups by HPLC as described in Example 3 and in FIG. 7. A2E-lipofuscin pigments were greatest in the animals receiving all-trans-retinal (the control group). While animals receiving $C_{20}D_3$-all-trans-retinal had 35% less A2E-lipofuscin than animals receiving all-trans-retinal. Likewise, animals receiving Fenretinide or TDH had 49% and 31% less A2E-lipofuscin compared to animals administered only all-trans-retinal.

CITED DOCUMENTS

The following documents, which have been cited above, are incorporated by reference as if recited in full herein:
1. Friedman, D. S.; O'Colmain, B. J.; Muñoz, B.; Tomany, S. C.; McCarty, C.; DeJong, P. T. V. M.; Nemesure, B.; Mitchell, P.; Kempen, J.; Congdon, N. Prevelance of age related macular degeneration in the United States. Arch. Ophthalmol. 2004, 122, 564-572.
2. Rattner, A.; Nathans, J. Macular degeneration: recent advances and therapeutic opportunities. Nat. Rev. Neurosci. 2006, 7, 860-872.
3. Jong, P. T. V. M. d. Age-related macular degeneration N. Engl J Med 2006, 355, 478-485.

4. Fine, S. L.; Berger, J. W.; Maguire, M. G.; Ho, A. G. Age-related macular degeneration N Engl J Med 2007, 342, 483-492.
5. Jarc-Vidmar, M.; Kraut, A.; Hawlina, M. Fundus autofluorescence imaging in Best's vitelliform dystrophy. Klinische Monatsblatter Fur Augenheilkunde 2003, 220, 861-867.
6. Capon, M.; Marshall, J.; Krafft, J.; Alexander, R.; Hiscott, P.; Bird, A. Sorsby's fundus dystrophy: a light and electron microscopic study. Ophthalmology 1989, 95, 1969-1977.
7. Chong, N.; Alexander, R.; Gin, T.; Bird, A.; Luthert, P. TIMP-3 collagen, and elastin immunohistochemistry and histopathology of Sorsby's fundus dystrophy Invest Ophthamol Vis Sci 2000, 41, 898-902.
8. Alikmets, R.; Singh, N.; Sun, H.; Shroyer, N. F.; Hutchinson, A.; Chidambaram, A.; Gerrard, B.; Baird, L.; Stauffer, D.; Peiffer, A.; Rattner, A.; Smallwood, P.; Li, Y.; Anderson, K. L.; Lewis, R. A.; Nathans, J.; Leppert, M.; Dean, M.; R., L. J. A Photoreceptore cell-specific ATP-binding transporter gene (ABCR) is mutated in recessive Stargardt macular dystrophy. Nat. Genet. 1997, 15, 236-246.
9. Haralampus-Grynaviski, N. M.; Lamb, L. E.; Clancy, C. M. R.; Skumatz, C.; Burke, J. M.; Sarna, T.; Simon, J. D. Spectroscopic and morphological studies of human retinal lipofuscin granules. Proc. Natl. Acad. Sci. U.S.A. 2003, 100.
10. Marmorstein, A. D.; Marmorstein, L. Y.; Sakaguchi, H.; Hollyfield, J. G. Spectral Profiling of Autofluorescence Associated with Lipofuscin, Bruch's Membrane, and Sub-RPE Deposits in Normal and AMD Eyes. Invest. Ophthalmol. Vis. Sci. 2002, 43, 2435-2441.
11. Smith, R. T.; Chan, J. K.; Busuoic, M.; Sivagnanavel, V.; Bird, A. C.; Chong, N. V. Autofluorescence characteristics of early, atrophic, and high-risk fellow eyes in age-related macular degeneration. Invest Ophthalmol Vis Sci. 2006, 47, 5495-5504.
12. Sakai, N.; Decatur, J.; Nakanishi, K.; Eldred, G. E. A2-E": An Unprecedented Pyridinium Bisretinoid. J. Am. Chem. Soc. 1996, 118, 1559-1560.
13. Fishkin, N. E.; Sparrow, J. R.; Allikements, R.; Nakanishi, K. Isolation and characterization of retinal pigment epithelial cell fluorophore: An all-trans-retinal dimer conjugate. Proc. Natl. Acad. Sci. U.S.A. 2005, 100, 7091-7096.
14. Sparrow, J. S.; Nakanishi, K.; Parish, C. A. The lipofuscin fluorophore A2E mediates blue light-induced damage to retinal pigmented epithelial cells. Invest. Ophthamol. Vis. Sci. 2000, 41, 1981-1989.
15. Suter, M.; Reme, C. E.; Christian Grimm; Wenzel, A.; Jaattela, M.; Esser, P.; Kociok, N.; Leist, M.; Richter, C. Age-related Macular Degeneration: The lipofuscin component n-retinyl-n-retinylidene ethanolamine detaches proapoptotic proteins from mitochondria and induces apoptosis in mammalian retinal pigment epithelial cells. J. Bio. Chem. 2000, 275, 39625-39630.
16. Finnemann, S.; Leung, L. W.; Rodriguez-Boulan, E. The lipofuscin component A2E selectively inhibits phagolysosomal degradation of photoreceptor phospholipid by the retinal pigment epithelium. Proc Natl Acad Sci USA. 2002, 99, 3842-3847.
17. De, S.; Sakmar, T. P. Interaction of A2E with model membranes. Implications to the pathogenesis of age-related macular degeneration. J Gen Physiol. 2002, 120, 147-157.
18. Bergmann, M.; Schütt, F.; Holz, F. G.; Kopitz, J. Inhibition of the ATP-driven proton pump in RPE lysosomes by the major lipofuscin fluorophore A2-E may contribute to the pathogenesis of age-related macular degeneration. FASEB J. 2004, 18, 562-564.
19. Radu, R. A.; Mata, N. L.; Bagla, A.; Travis, G. H. Light exposure stimulates formation of A2E oxiranes in a mouse model of Stargardt's macular degeneration. Proc Natl Acad Sci USA. 2004, 101, 5928-5933.
20. Ben-Shabat, S.; Parish, C. A.; Hashimoto, M.; Liu, J.; Nakanishi, K.; Sparrow, J. R. Fluorescent pigments of the retinal pigment epithelium and age-related macular degeneration. Bioorg Med Chem Lett. 2001, 11, 1533-1540.
21. Schutt, F.; Bergmann, M.; Holz, F. G.; Dithmar, S.; Volcker, H.-E.; Kopitz, J. Accumulation of A2-E in mitochondrial membranes of cultured RPE cells. 2007, 245, 391-398.
22. Schutt, F.; Davies, S.; Kopitz, J.; Holz, F. G.; Boulton, M. E. Photodamage to human RPE cells by A2-E, a retinoid component of lipofuscin. 41 2000, 2303-2308.
23. Maiti, P.; Kong, J.; Kim, S. A.; Sparrow, J. S.; Allikmets, R.; Rando, R. R. SamII molecule RPE65 antagonists limit the visual cycle and prevent lipofuscin formation. Biochemistry 2006, 45, 852-860.
24. Radu, R. A.; Mata, N. L.; Nusinowitz, S.; Liu, X.; Sieving, P. A.; Travis, G. H. Treatment with isotretinion inhibits lipofuscin accumulation in a mouse model of recessive Stargardt macular degeneration. Proc. Natl. Acad. Sci. U.S.A. 2003, 100, 4742-4747.
25. Golczak, M.; Maeda, A.; Bereta, G.; Maeda, T.; Kiser, P. D.; Hunzelmann, S.; Lintig, J. V.; Blaner, W. S.; Palczewski, K. Metabolic Basis of Visual Cycle Inhibition by Retinoid and Nonretinoid Compounds in the Vertebrate Retina. J. Biol. Chem. 2008, 283, 9543-9554.
26. Katz, M. L.; Drea, C. M.; Robison, W. G. Relationship between dietary retinol and lipofuscin in the retinal pigment epithelium. Mech. Age. Dev. 1986, 35, 291-305.
27. Radu, R. A.; Han, Y.; Bui, T. V.; Nusinowitz, S.; Bok, D.; Lichter, J.; Widder, K.; Travis, G. H.; Mata, N. L. Reductions in serum vitamin A arrest Accumulation of toxic retinal fluorophores: A potential therapy for treatment of lipofuscin based retinal diseases. Invest Ophthamol Vis Sci 2005, 46, 4393-4401.
28. Wassell, J.; Boulton, M. A role for vitamin A in the formation of ocular lipofuscin. Br J Ophthalmol 1997, 81, 911-918.
29. Owsley, C.; Jackson, G. R. Aging and scotopic dysfunction. Perception 2000, 29, Abstract Supplement.
30. Owsley, C.; Jackson, G. R.; White, M.; Feist, R.; Edwards, D. Delays in rod-mediated dark adaptation in early age-related maculopathy. Ophthalmology 2001, 108, 1196-1202.
31. Baehr, W.; Wub, S. M.; Birdc, A. C.; Palczewski, K. The retinoid cycle and retina disease. Vision Research 2003, 43, 2957-2958.
32. Maeda, A.; Maeda, T.; Golczak, M.; Imanishi, Y.; Leahy, P.; Kubota, R.; Palczewski, K. Effects of potent inhibitors of the retinoid cycle on visual function and photoreceptor protection from light damage in mice. Mol. Pharmacol. 2006, 70, 1220-1229.
33. Hong, W. K.; Itri, L. M. *Retinoids and human cancer*, Second Edition Ed.; Raven Press Ltd: New York, 1994.
34. Gudas, L. J.; Sporn, M. B.; Roberts, A. B. *Cellular biology and biochemistry of retinoids*; Raven Press Ltd.: New York, 1994; 443-520 pp.

35. Nason-Burchenal, K.; Dmitrovsky, E. *The retinoids: cancer therapy and prevention mechanisms*: Berlin, 1999; 301-322 pp.
36. Dragnev, K. H.; Rigasa, J. R.; Dmitrovsky, E. The Retinoids and Cancer Prevention Mechanisms Oncologist 2003, 5, 361-368.
37. Freemantle, S. J.; Spinella, M. J.; Dmitrovsky, E. Retinoids in cancer therapy and chemoprevention: promise meets resistance. Oncogene 2003, 22, 7305-7315.
38. Soriatan, RXlist.com, http://www.rxlist.com/cgi/generic/acitretin.htm#, accessed Sep. 2, 2008. 2008.
39. Targretin, RXlist.com http://www.rxlist.com/cgi/generic/bexarotene.htm, accessed Sep. 2 2008.
40. Acutane, RXlist.com, http://www.rxlist.com/cgi/generic/isotret.htm, accessed Sep. 2 2008.
41. Camerini, T.; Mariani, L.; Palo, G. D.; Marubini, E.; Mauro, M. G. D.; Decens, A.; Costa, A.; Veronesi, U. Safety of the Synthetic Retinoid Fenretinide: Long-Term Results From a Controlled Clinical Trial for the Prevention of Contralateral Breast Cancer. J. Clin. Oncol. 2001, 19, 1664-1670.
42. Puduvalli, V. K.; Yung, W. K. A.; Hess, K. R.; Kuhn, J. G.; Groves, M. D.; Levin, V. A.; Zwiebel, J.; Chang, S. M.; Cloughesy, T. F.; Junck, L.; Wen, P.; Lieberman, F.; Conrad, C. A.; Gilbert, M. R.; Meyers, C. A.; Liu, V.; Mehta, M. P.; Nicholas, M. K.; Prados, M. Phase II Study of Fenretinide (NSC 374551) in Adults With Recurrent Malignant Gliomas: A North American Brain Tumor Consortium Study. J. Clin. Oncol. 2004, 22, 4282-4289.
43. Villablanca, J. G.; Khan, A. A.; Avramis, V. I.; Seeger, R. C.; Matthay, K. K.; Ramsay, N. K.; Reynolds, C. P. Phase I trial of 13-cis-retinoic acid in children with neuroblastoma following bone marrow transplantation. J Clin Oncol. 1995, 13, 849-901.
44. Chemotherapy drugs, Isorettinoin, http://www.chemocare.com/bio/isotretinoin.asp, accessed Sep. 8 2008.
45. Haskell, M.; Mazumder, R. M.; Peerson, J. M.; Jones, A. D.; Wahed, M. A.; Mahalanabis, D.; Brown, K. H. Use of deuterated-retinol-dilution technique to assess total body vitamin A stores of adult volunteers consuming different amounts of vitamin A 1, 2, 3. Amer. J. of Clinical Nutrition 1999, 70, 874-880.
46. Bausch, J.; Rietz, P. Method for the assessment of vitamin A liver stores. Acta Vitaminol Enzymol 1977, 31, 99-112.
47. Pardoen, J. A.; Mulder, P. P. J.; Van den Berg, E. M. M.; Lugtenburg, J. Synthesis of 8-, 9-, 12-, and 13-mono-13C-retinal. Canadian Journal of Chemistry 1985, 63, 1431-1435.
48. Weng, J.; Mata, N. L.; Azarian, S. M.; Tzekov, R. T.; Birch, D. G.; Travis, G. H. Insights into the function of Rim protein in photoreceptors and etiology of Stargardt's disease from the phenotype in abcr knockout mice. Cell 1999, 9, 13-23.
49. Kim, S.; Fishkin, N.; Kong, J.; Nakanishi, K.; Allikmets, R.; Sparrow, J. R. Rpe65 Leu450Met variant is associated with reduced levels of the retinal pigment epithelium lipofuscin fluorophores A2E and iso-A2E. Proc. Natl. Acad. Sci. U.S.A. 2004, 101, 11668-11672.
50. Soo-Jong; Kwon, Y.-J.; Han, H.-S.; Park, S.-H.; Park, M.-S.; Rho, Y.-S.; Sin, H.-S. Synthesis and Biological Activity of Novel Retinamide and Retinoate Derivatives. Chemical & Pharmaceutical Bulletin 2004, 52, 501-506.

The scope of the present invention is not limited by the description, examples, and suggested uses herein and modifications can be made without departing from the spirit of the invention. Thus, it is intended that the present invention cover modifications and variations of this invention provided that they come within the scope of the appended claims and their equivalents.

What is claimed is:

1. A pharmaceutical composition comprising a substituted $C_{20}$-$D_{1-3}$-retinoid and a pharmaceutically acceptable carrier, wherein the $C_{20}$-$D_{1-3}$-retinoid is selected from the group consisting of $C_{20}$-$D_{1-3}$-retinol, $C_{20}$-$D_{1-3}$-retinol ester, $C_{20}$-$D_{1-3}$-retinal and a $C_{20}$-$D_{1-3}$-pro-vitamin A carotenoid.

2. The pharmaceutical composition according to claim 1, wherein the substituted $C_{20}$-$D_{1-3}$-retinoid is selected from the group consisting of $C_{20}$-$D_3$-retinol, $C_{20}$-$D_3$-retinol ester, $C_{20}$-$D_3$-retinal and a $C_{20}$-$D_3$-pro-vitamin A carotenoid.

3. The pharmaceutical composition according to claim 2, wherein the $C_{20}$-$D_{1-3}$-retinoid is $C_{20}$-$D_3$-retinol acetate.

4. The pharmaceutical composition according to claim 1, wherein the pharmaceutical composition is in unit dosage form.

5. The pharmaceutical composition according to claim 1, wherein the $C_{20}$-$D_{1-3}$-retinoid, corresponding to the aldehyde of the $C_{20}$-$D_{1-3}$-retinol acetate, forms A2E in vitro about 7 times slower than non-deuterium-enriched retinoid.

6. The pharmaceutical composition according to claim 1, wherein the $C_{20}$-$D_{1-3}$-retinoid inhibits the formation of A2E and/or ATR-dimer compared with the corresponding non-deuterium enriched retinoid.

7. The pharmaceutical composition according to claim 1, further comprising an effective amount of a supplement selected from the group consisting of (2E,6E)-N-hexadecyl-3,7,11-trimethyldodeca-2,6,10-trienamine, (12E,16E)-13,17,21-trimethyldocosa-12,16,20-trien-11-one, 13-cis-retinoic acid, all-trans-retinylamine, and fenretinide, and combinations thereof.

8. The pharmaceutical composition according to claim 1, further comprising one or more additives.

9. The pharmaceutical composition according to claim 8, wherein the additives are selected from the group consisting of zinc, vitamin E, vitamin D, and combinations thereof.

10. The pharmaceutical composition according to claim 9, wherein the zinc is present in the pharmaceutical composition at between about 3 to about 80 mg.

11. The pharmaceutical composition according to claim 9, wherein the zinc is present in the pharmaceutical composition at between about 3 to about 10 mg.

12. The pharmaceutical composition according to claim 9, wherein the zinc is present in the pharmaceutical composition at between about 10 to about 80 mg.

13. The pharmaceutical composition according to claim 9, wherein the vitamin E is present in the pharmaceutical composition at between about 3 to about 3,000 mg.

14. The pharmaceutical composition according to claim 9, wherein the vitamin E is present in the pharmaceutical composition at between about 3 to about 15 mg.

15. The pharmaceutical composition according to claim 9, wherein the vitamin E is present in the pharmaceutical composition at between about 15 to about 3,000 mg.

16. The pharmaceutical composition according to claim 9, wherein the vitamin D is present in the pharmaceutical composition at between about 0.005 to about 0.1 mg.

17. The pharmaceutical composition according to claim 9, wherein the vitamin D is present in the pharmaceutical composition at between about 0.005 to about 0.015 mg.

18. The pharmaceutical composition according to claim 9, wherein the vitamin D is present in the pharmaceutical composition at between about 0.015 to about 0.1 mg.

19. The pharmaceutical composition according to claim 1, wherein the substituted $C_{20}$-$D_{1-3}$-retinoid is present in the pharmaceutical composition at a level sufficient to deliver on average about 0.1 to about 90 mg/day to a patient.

20. The pharmaceutical composition according to claim 1, wherein the pharmaceutical composition comprises an additional active.

21. The pharmaceutical composition according to claim 20, wherein the additional active is selected from the group consisting of eye antioxidants, minerals, negatively-charged phospholipids, carotenoids, and combinations thereof.

22. The pharmaceutical composition according to claim 21, wherein the eye antioxidant is selected from the group consisting of vitamin C, vitamin E, beta-carotene, coenzyme Q, OT-551, 4-hydroxy-2,2,6,6-tetramethylpiperidine-N-oxyl, butylated hydroxytoluene, resveratrol, a trolox analog (PNU-83836-E), bilberry extract, and combinations thereof.

23. The pharmaceutical composition according to claim 21, wherein the mineral is selected from the group consisting of cupric oxide, zinc oxide; selenium-containing compounds, and combinations thereof.

24. The pharmaceutical composition according to claim 21, wherein the negatively-charged phospholipid is selected from the group consisting of cardiolipin, phosphatidylglycerol, and combinations thereof.

25. The pharmaceutical composition according to claim 1, wherein the carotenoid is selected from the group consisting of zeaxanthin, lutein, and combinations thereof.

26. The pharmaceutical composition according to claim 1, wherein the pharmaceutical composition is suitable for administration directly to the eye.

27. The pharmaceutical composition according to claim 1, wherein the pharmaceutical composition is suitable for use as nutraceutical composition.

28. The pharmaceutical composition according to claim 3, wherein the $C_{20}$-$D_{1-3}$-retinoid, corresponding to the aldehyde of the $C_{20}$-$D_{1-3}$-retinol acetate, forms A2E in vitro about 7 times slower than non-deuterium-enriched retinoid.

* * * * *

(12) INTER PARTES REVIEW CERTIFICATE (3964th)
United States Patent (10) Number: US 9,486,432 K1
Washington (45) Certificate Issued: Apr. 22, 2025

(54) COMPOSITIONS AND METHODS FOR TREATING MACULAR DEGENERATION

(71) Applicant: The Trustees of Columbia University in the City of New York

(72) Inventor: Ilyas Washington

(73) Assignee: The Trustees of Columbia University in the City of New York

Trial Number:

IPR2024-00312 filed Dec. 19, 2023

Inter Partes Review Certificate for:

Patent No.: 9,486,432
Issued: Nov. 8, 2016
Appl. No.: 14/510,975
Filed: Oct. 9, 2014

The results of IPR2024-00312 are reflected in this inter partes review certificate under 35 U.S.C. 318(b).

INTER PARTES REVIEW CERTIFICATE
U.S. Patent 9,486,432 K1
Trial No. IPR2024-00312
Certificate Issued Apr. 22, 2025

AS A RESULT OF THE INTER PARTES REVIEW PROCEEDING, IT HAS BEEN DETERMINED THAT:

Claims 1-28 are cancelled.

* * * * *